(12) United States Patent
Thastrup et al.

(10) Patent No.: US 8,318,717 B2
(45) Date of Patent: Nov. 27, 2012

(54) COMPOUNDS MODIFYING APOPTOSIS

(75) Inventors: Ole Thastrup, Birkerod (DK); Jens Chr. Norrild, Birkerod (DK)

(73) Assignee: 2cureX, Birkerod (DK)

( * ) Notice: Subject to any disclaimer, the term of this patent is extended or adjusted under 35 U.S.C. 154(b) by 918 days.

(21) Appl. No.: 11/914,994

(22) PCT Filed: May 23, 2006

(86) PCT No.: PCT/DK2006/000280
§ 371 (c)(1),
(2), (4) Date: Apr. 24, 2008

(87) PCT Pub. No.: WO2006/128455
PCT Pub. Date: Dec. 7, 2006

(65) Prior Publication Data
US 2008/0194537 A1    Aug. 14, 2008

(30) Foreign Application Priority Data

May 25, 2005  (DK) .................................. 2005 00763
May 25, 2005  (WO) ................ PCT/DK2005/000347
Nov. 25, 2005  (DK) .................................. 2005 01663

(51) Int. Cl.
*A61K 31/397* (2006.01)
*C07C 233/00* (2006.01)
*C07D 207/16* (2006.01)

(52) U.S. Cl. .................................. 514/210.18; 548/537
(58) Field of Classification Search ...................... None
See application file for complete search history.

(56) References Cited

FOREIGN PATENT DOCUMENTS

| EP | 0695757 | 12/1996 |
|----|---------|---------|
| WO | WO 02 096930 | 12/2002 |
| WO | WO2004/005248 | 1/2004 |
| WO | WO2004/072105 | 8/2004 |
| WO | WO 2005/116643 | 12/2005 |
| WO | WO2005/116656 | 12/2005 |

OTHER PUBLICATIONS

Cohen et al, Bioorg. Med. Chem. Lett., 20, 2010, 2229-2233.*
Sharma et al., caplus an 2004:41435.*
Bauer et al., caplus an 1976:146146759.*
McRae Brian et al. Biochemistry, vol. 19, 1980 3973-3978.
Kipp et al. Biochemestry, vol. 41, No. 23, 2002 p. 7344-7349.
Groth et al. Combination Chemistry & High Throughput Screening, 2003, vol. 6, No. 7 p. 589-610.

* cited by examiner

*Primary Examiner* — Sun Jae Loewe
(74) *Attorney, Agent, or Firm* — Gifford, Krass, Sprinkle, Anderson & Citkowski, P.C.

(57) ABSTRACT

The present invention relates to compounds capable of inhibiting binding of the Smac protein to Inhibitors of apoptosis (IAPs). Such compounds are preferably capable of inhibiting IAP and thus may promote apoptosis or sensitize cells for apoptosis. The compounds may be used in the treatment of proliferative diseases, such as cancer.

3 Claims, 6 Drawing Sheets

Step 1: Reductive coupling of 5 phenylethylamines

13

14

15

16

17

19

20

COMPOUNDS MODIFYING APOPTOSIS

All patent and non-patent references cited in the application are hereby incorporated by reference in their entirety.

FIELD OF INVENTION

The present invention relates to compounds capable of inhibiting binding of the Smac protein to Inhibitors of apoptosis (IAPs). Such compounds are preferably capable of inhibiting IAP and thus may promote apoptosis or sensitize cells for apoptosis.

The compounds may be used in the treatment of proliferative diseases, such as cancer.

BACKGROUND OF INVENTION

Programmed cell death plays a critical role in regulating cell number and in eliminating stressed or damaged cells from normal tissues. Indeed, the network of apoptotic signalling mechanisms inherent in most cell types provides a major barrier to the development and progression of human cancer. Since most commonly used radiation and chemo-therapies rely on activation of apoptotic pathways to kill cancer cells, tumour cells which are capable of escaping programmed cell death often become resistant to treatment.

Apoptosis is generally mediated by a class of proteases known as Caspases. Once activated, Caspases cleave a number of cell death-related substrates, effecting destruction of the cell.

Tumour cells have devised a number of strategies to circumvent apoptosis. One recently reported molecular mechanism involves the overexpression of members of the IAP family. IAPs sabotage apoptosis by directly interacting with and neutralizing Caspases. One IAP, XIAP, has three functional domains referred to as BIR 1, 2 & 3 domains. BIR3 interacts directly with Caspase 9 and inhibits its ability to bind and cleave its natural substrate, Procaspase 3. Another prominent IAP is ML-IAP (also referred to as Livin), which comprises one BIR domain.

It has been reported that a proapoptotic mitochondrial protein, Smac (also known as DIABLO), is capable of neutralizing XIAP by binding to a peptide binding pocket (Smac binding site) on the surface of BIR3 thereby precluding interaction between XIAP and Caspase 9. Smac also interacts with the BIR domain of ML-IAP.

In the absence of IAP-Caspase 9 binding, apoptosis mediated through the action of Caspase 3/7 may be initiated.

WO2004/005248 (Novartis) describes XIAP inhibitor compounds. The compounds compete with Smac for binding to GST-BIR3 (see p. 21). In a model system using cells requiring XIAP for survival after TRAIL exposure these compounds overcome XIAP-dependent TRAIL resistance at concentrations in the range of 0.4 to 0.9 μM.

However, these compounds are only moderately efficient as evidenced by the moderate XIAP binding and their moderate ability to induce apoptosis and the growth of cancer cells in vivo.

SUMMARY OF INVENTION

There exists therefore an unmet need for compounds capable of binding XIAP and/or ML-IAP very efficiently. In particular, there is a need for compounds capable of inducing apoptosis for example in rapidly dividing cells. Such compounds are useful for the treatment of proliferative diseases, including cancer.

It is thus an object of the present invention to provide compounds of the general formulae

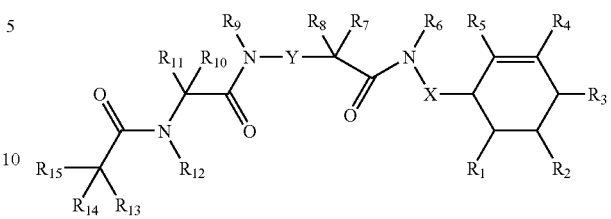

wherein $R_1$, $R_2$, $R_3$, $R_4$ and $R_5$ individually are selected from the group consisting of —H, halide, $C_{1-6}$ alkyl, hydroxyl, $C_{1-6}$ alkoxy, $SR_{21}$, $S(O)R_{21}$, $SO_2R_{21}$, $NH_2$, $NHR_{21}$, $NR_{21}R_{22}$, CN, CHO, COOH, $COOR_{21}$, $CONH_2$, $CONHR_{21}$, $CONR_{21}R_{22}$ and $C_{1-6}$ alkyl substituted with halide or hydroxyl or amine, or $R_1$ and $R_2$ together forms a 4 to 8 membered aromatic or aliphatic ring which may contain heteroatoms, or $R_2$ and $R_3$ together forms a 4 to 8 membered aromatic or aliphatic ring which may contain heteroatoms, or $R_3$ and $R_4$ together forms a 4 to 8 membered aromatic or aliphatic ring which may contain heteroatoms, or $R_4$ and $R_6$ together forms a 4 to 8 membered aromatic or aliphatic ring which may contain heteroatoms, and X is $(CH_2)_n$, wherein n is an integer in the range of 0 to 5 or $C_{1-5}$ alkyl substituted with an amide; or X in one embodiment forms a ring with $R_6$ as described below; and Y is $(CH_2)_n$, wherein n is an integer in the range of 0 to 2; and $R_6$ is H or a linker covalently linked to a solid support; or in one embodiment $R_6$ and X together form an aliphatic ring including the N atom to which $R_6$ is attached; and $R_7$ and $R_9$ together forms a 4 to 6 membered ring or 6 to 14 membered fused ring system, which optionally may be substituted with phenyl, $NHR_{16}$, $NR_{17}R_{18}$ or —NH—CO—$R_{16}$, wherein $R_{16}$ is selected from the group consisting of 3 to 6 membered aliphatic or aromatic rings, halide, $C_{1-6}$ linear or branched alkyl and $C_{1-6}$ alkyl substituted with any of the aforementioned, $R_{17}$ and $R_{18}$ individually is selected from the group consisting of 3 to 6 membered aliphatic or aromatic rings, halide, $C_{1-6}$ linear or branched alkyl and $C_{1-6}$ alkyl substituted with any of the aforementioned; and $R_8$ is —H or phenyl; or $R_7$ and $R_8$ together forms a 4 to 6 membered ring, which optionally may be substituted with $C_{1-6}$ alkyl, halid, $C_{1-6}$ alkyl halid, OH, OR, $NH_2$, NHR, $NHR_2$ and $R_9$ is —H; or $R_7$ and $R_8$ individually are selected from the group consisting of —H, 3 to 6 membered aliphatic and aromatic rings, and $R_9$ is —H; and $R_{10}$ and $R_{11}$ together forms a 4 to 6 membered ring and $R_{12}$ is —H, or $R_{10}$ and $R_{12}$ together forms a 4 to 6 membered ring and $R_{11}$ is —H, or $R_{10}$ and $R_{11}$ individually may be selected from the group consisting of $C_{1-6}$ linear and branched alkyl, $C_{1-6}$ alcohol, $C_{1-6}$ alkoxy, 3 to 6 membered aliphatic and aromatic rings, $C_{2-6}$ carboxylic acids, $C_{2-6}$ esters, $C_{1-6}$ amides, —H, halide, $C_{2-6}$ ether or any of the aforementioned substituted with $C_{3-6}$ branched alkyl, halide, 3 to 6 membered aliphatic or aromatic rings, with the proviso that if $R_{10}$ or $R_{11}$ are isopropyl or tertbutyl, then X is $C_{1-5}$ alkyl substituted with an amide, preferably with —$CONH_2$; and $R_{13}$ and $R_{14}$ together forms a 4 to 6 membered ring and $R_{15}$ is —H; or $R_{13}$, $R_{14}$ and $R_{15}$ individually are selected from the group consisting of $C_{1-6}$ linear and branched alkyl, $C_{1-6}$ alkoxy, 3 to 6 membered aliphatic and aromatic rings, $C_{2-6}$ esters, halide, $C_{1-6}$ amide, amine, $C_{2-6}$ ether or any of the aforementioned substituted with $C_{3-6}$ branched alkyl, halide or 3 to 6 membered aliphatic or aromatic rings.

It is also an object of the invention to provide compounds of the general structure wherein X, Y, $R_6$, $R_7$, $R_8$, $R_9$, $R_{10}$, $R_{11}$, $R_{12}$, $R_{13}$, $R_{14}$ and $R_{15}$ are as defined herein above and $R_{23}$ is selected from the group consisting of heteroaromatic ring systems, aromatic ring systems and cyclo-alkyls, wherein any of the aforementioned may be substituted, preferably with $R_1$, $R_2$, $R_3$, $R_4$, $R_5$ and/or amide. Heteroaromatic ring systems may in a preferred embodiment be selected from the group consisting of $C_{5-8}$ heteroaromatic ring systems comprising S, more preferably comprising only one S, even more preferably they may be selected from the group consisting of wherein X is preferably attached at the position indicated by asterisk, and wherein said heteroaromatic ring in a very preferred embodiment is not substituted. Aromatic ring systems are preferably of the structure:

wherein X preferably is attached at the position indicated by asterisk and $R_1$, $R_2$, $R_3$, $R_4$ and $R_5$ are as indicated herein above.

It is an additional object of the invention to provide compound of the general structure $AA_1$-$AA_2$-$AA_3$-$AA_4$, wherein each of $AA_1$, $AA_2$, $AA_3$ and $AA_4$ are amino acids. The amino acids may be naturally occurring or not naturally occurring amino acids.

It is also an object of the invention to provide libraries comprising at least two different compounds according to the invention.

It is another object of the invention to provide methods of identifying a compound capable of interrupting binding between Smac and an inhibitor of apoptosis of the IAP-family such as XIAP or ML-IAP or other members of the IAP family or a Smac binding fragment thereof, wherein said fragment comprises the BIR-3 domain of XIAP or the BIR domain of ML-IAP, comprising the steps of
  a. Providing Smac
  b. Providing XIAP or ML-IAP or a Smac binding fragment thereof
  c. Contacting Smac and XIAP or ML-IAP or a Smac binding fragment thereof with a library according to any of Tables 6-9
  d. Identifying compounds capable of interrupting binding between Smac and XIAP or ML-IAP or a Smac binding fragment thereof.

DEFINITIONS

Figure 1:
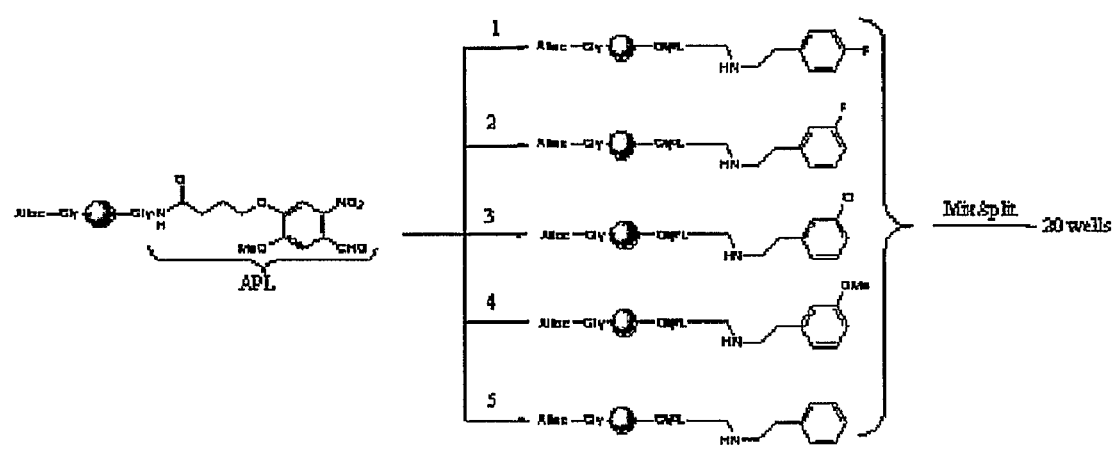
FIG. 1 illustrates the synthesis of a preferred library according to the invention.
Figure 2A:
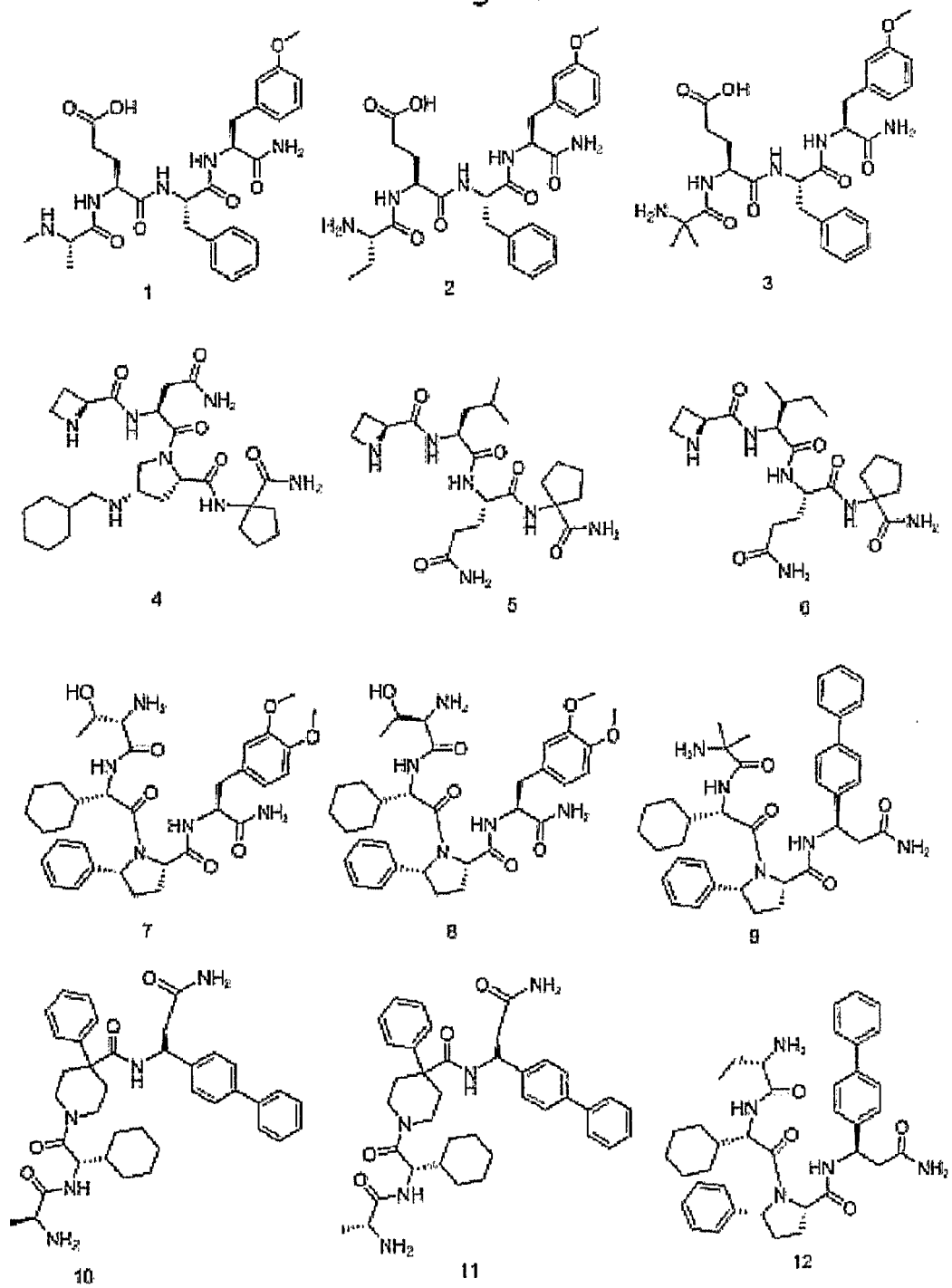
FIG. 2 illustrates examples of preferred compounds according to the invention.
Figure 2B:
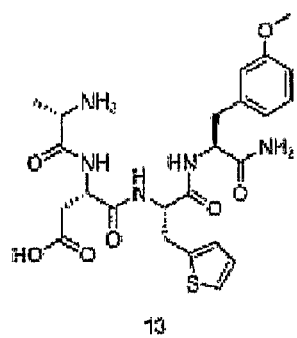
Figure 2B:
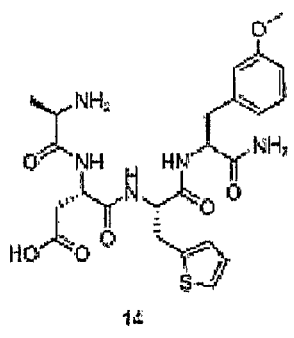
Figure 2B:
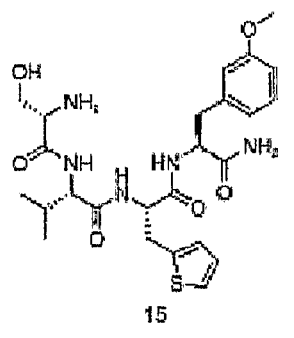
Figure 2B:
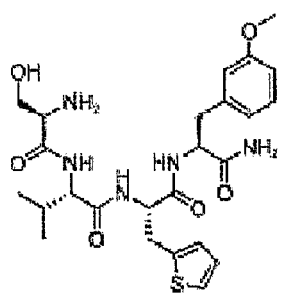
Figure 2B:
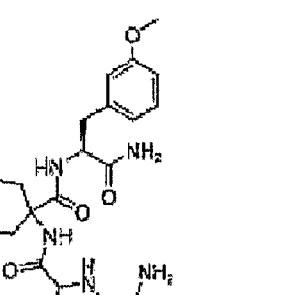
Figure 2B:
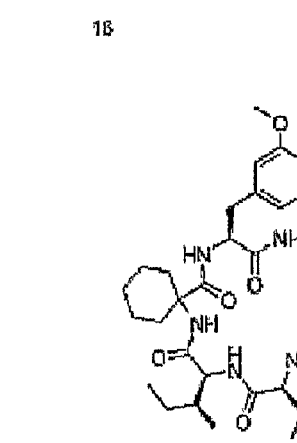
Figure 2B:
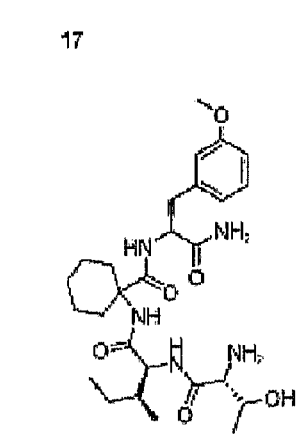

Naturally occurring amino acids are named herein using either their 1-letter or 3-letter code. If nothing else is specified amino acids may be of D or L-form. In the description (but not in the sequence listing) 3-letter codes starting with a capital letter indicate amino acids of L-form, whereas 3-letter codes in small letters indicate amino acids of D-form. Three- and one-letter abbreviations for amino acids are used according to the recommendations from IUPAC, see for example http://www.chem.qmw.ac.uk/iupac.

The term "a" as used herein, can mean one or more, depending on the context in which it is used.

The term "FRET" is used to describe the occurrence of Fluorescence resonance energy transfer between a fluorophore donor and an acceptor fluorophore. It is a distance-dependent interaction between the electronic excited states of two fluorophores in which excitation is transferred from a donor fluorophore to an acceptor fluorophore without emission of a photon. The efficiency of FRET is dependent on the inverse sixth power of the intermolecular separation, making it useful over distances comparable with the dimensions of biological macromolecules. Thus, FRET is an important technique for investigating interactions between cellular molecules for example complex formation.

The term "BRET" is used to describe a process that is related to FRET, but differs from FRET in that donor is a bioluminescent protein like luciferase that generates its own luminescence emission in the presence of a substrate, and that can pass the energy to an acceptor fluorophore. For either BRET or FRET to work, the donor's emission spectrum must overlap the acceptor's absorption spectrum, their transition dipoles must be in an appropriate orientation, and the donor and acceptor must be in close proximity (usually within 30-80 Å of each other, depending on the degree of spectral overlap).

The term "mammalian cell" is intended to indicate any cell of mammalian origin. The cell may be an established cell line, many of which are available from The American Type Culture Collection (ATCC, Virginia, USA) or a primary cell with a limited life span derived from a mammalian tissue, including tissues derived from a transgenic animal, or a newly established immortal cell line derived from a mammalian tissue including transgenic tissues, or a hybrid cell or cell line derived by fusing different cell types of mammalian origin e.g. hybridoma cell lines. The cells may optionally express one or more non-native gene products, e.g. receptors.

The term "comprising" should be understood in an inclusive manner. Hence, by way of example, a composition comprising compound X, may comprise compound X and optionally additional compounds.

The term "multiple" should be understood as "at least two".

The term "library of test compounds" should be understood as a collection of test compounds comprising at least 2 different test compounds.

The term split/mix refer herein to the process of i) dividing a bead assembly into portions and reacting each portions with a different building block followed by mixing the resin into one portion providing an even distribution throughout the assembly of beads containing said building blocks, ii) preparing (activating) the resin for attachment of the next building block and repeating the process n times of dividing, reacting, mixing and activating, thus providing an exponential growth of the number ($m^n$) of distinct molecular entities of complexity n each attached to separate beads.

The term "one bead-one compound library" refers to libraries immobilised on resin beads, wherein each individual resin bead does not comprise more than one library member in one or multiple copies. In a particular form of such libraries each member is represented by multiple fragments of said member obtained by ladder synthesis encoding.

The term "one bead-two compound library" refers to libraries immobilised on resin beads, wherein each individual resin bead does not comprise more than one library member in one or multiple copies and wherein each individual resin bead in addition to said library member also comprises an adhesion compound.

The term "cleavable linker" is used to describe any chemical moiety which may be used to attach any molecule to a solid support either covalently or via complex formation and thereafter release said molecule by the action of either acid, base, electrophiles, nucleophiles, oxidative agents, reductive agents, metals, heat or light.

The term "n"-membered ring, relates to an aliphatic or aromatic ring, wherein n atoms forms the ring per se. The n atoms are selected from the group consisting of C, S, O and N. Each atom in the ring may be substituted. Thus by way of example benzene and fluorobenzene are considered 6 membered rings.

As used herein, the term "library" means a collection of molecular entities or test compounds, herein also designated "library compounds".

When no specific stereoisomer of a compound is indicated then any given formulae or name is meant to cover all stereoisomers covered by the particular formulae or name.

DETAILED DESCRIPTION OF THE INVENTION

Compounds

The present invention relates to compounds of the general formulae

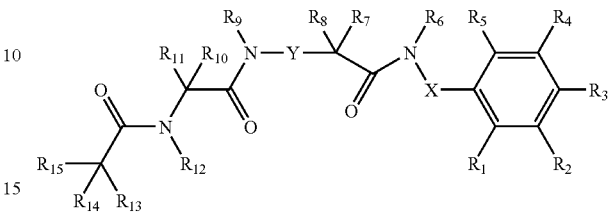

In another embodiment the present invention relates to compounds of the general formulae

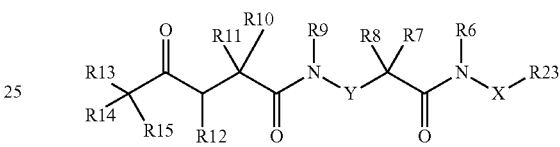

wherein $R_{23}$ in one embodiment may be

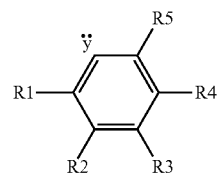

The following description of preferred R, X and Y groups relates to both general structures.

$R_1, R_2, R_3, R_4$ and $R_5$ may individually be selected from the group consisting of —H, halide, $C_{1-6}$ alkyl, hydroxyl, $C_{1-6}$ alkoxy, $SR_{21}$, $S(O)R_{21}$, $SO_2R_{21}$, $NH_2$, $NHR_{21}$, $NR_{21}R_{22}$, CN, CHO, COOH, COOR$_{21}$, CONH$_2$, CONHR$_{21}$, CONR$_2$, R$_{22}$ and $C_{1-6}$ alkyl substituted with halide or hydroxyl or amine. $R_{21}$ and $R_{22}$ may individually be selected from the group consisting of —H, $C_{1-6}$ alkyl, —OH, $C_{1-6}$ alkyl hydroxyl, $C_{1-6}$ alkyl halid, $C_{1-6}$ alkoxy, $C_{1-6}$ amino alkyl and $NH_2$.

Preferably $R_1, R_2, R_3, R_4$ and $R_5$ are hydrophobic groups. In one preferred embodiment $R_1, R_2, R_3, R_4$ and $R_5$ may individually be selected from the group consisting of —H, halide, $C_{1-6}$ alkyl, $C_{1-6}$ alkoxy, and $C_{1-6}$ alkyl substituted with halide. For example 1, such as 2, for example 3, such as 4, for example all of $R_1, R_2, R_3, R_4$ and $R_5$ be selected from the group consisting of halide, $C_{1-6}$ alkyl, $C_{1-6}$ alkoxy, and $C_{1-6}$ alkyl substituted with halide, whereas the others may be —H. Halide may in this context preferably be —F or —Cl. Thus for example 1, such as 2, for example 3, such as 4, for example all of $R_1, R_2, R_3, R_4$ and $R_5$ may be halide selected from the group consisting of —F and —Cl, whereas the others be —H. In another embodiment for example 1, such as 2, for example 3, such as 4, for example all of $R_1, R_2, R_3, R_4$ and $R_5$ may be $C_{1-6}$ alkoxy, such as $C_{1-3}$ alkoxy, for example $C_{1-2}$ alkoxy, such as methoxy, whereas the others may be —H.

It is also possible that one or more of $R_1$, $R_2$, $R_3$, $R_4$ and $R_5$ form a ring. Accordingly, $R_1$ and $R_2$ may together form a 4 to 8 membered aromatic or aliphatic ring which may contain heteroatoms, and/or $R_2$ and $R_3$ may together form a 4 to 8 membered aromatic or aliphatic ring which may contain heteroatoms, and/or $R_3$ and $R_4$ together forms a 4 to 8 membered aromatic or aliphatic ring which may contain heteroatoms, and/or $R_4$ and $R_5$ together forms a 4 to 8 membered aromatic or aliphatic ring which may contain heteroatoms.

Preferably, only one, such as at the most two of $R_1$ and $R_2$, $R_2$ and $R_3$, $R_3$ and $R_4$ or $R_4$ and $R_5$ together forms a ring. The ring may be 4 to 8 membered, preferably, it is 4 to 6 membered, such as 6 membered. It may contain heteroatoms, such as N, S or O, preferably at the most 2, such as at the most 1 heteroatom. Thus, X may be connected to a multicyclic ring system, such as naphthalene, tetrahydronaphthalene, quinoline, tetrahydroquinoline or any of the aforementioned substituted with any group, preferably a hydrophobic group, such as $C_{1-6}$ alkyl, $C_{1-6}$ alkoxy, and $C_{1-6}$ alkyl substituted with halide.

In preferred embodiment of the invention $R_1$ is —H.

In a preferred embodiment of the invention $R_2$ is selected from the group consisting of —H and $C_{1-6}$ alkoxy, more preferably from the group consisting of —H and methoxy.

In a preferred embodiment of the invention $R_3$ is selected from the group consisting of —H, $C_{1-6}$ alkoxy, and phenyl, more preferably from the group consisting of —H, methoxy and phenyl.

In a preferred embodiment of the invention $R_4$ is —H.

In a preferred embodiment of the invention $R_5$ is —H.

X may be $(CH_2)_n$, wherein n is an integer in the range of 0 to 5, preferably 1 to 3, more preferably 2 or X may be $C_{1-5}$ alkyl substituted with an amide, such as an $C_{0-5}$ amide, preferably X may be $C_{1-5}$ alkyl substituted with —$CONH_2$, more preferably X may be —$CH(CONH_2)$—$CH_2$. The term $C_{0-5}$ amide cover substituents of the formulae $(CH_2)_n$—$CONH_2$, wherein n is 0 to 5.

In a preferred embodiment of the invention X is selected from the group consisting of —$CH(CONH_2)$—$CH_2$— and —CH—$CH_2CONH_2$ wherein the CH group is linked to N and the phenyl group, In embodiments of the invention wherein the compounds are immobilised on a solid support, such as a resin bead, they may be attached to said solid support via the X group, for example via the amide group of X. In these embodiments X will thus rather than comprising a free —$NH_2$ group of an amide be covalently linked via the amine-group to a solid support, optionally through a linker, such as a cleavable linker as described herein below.

$R_6$ may be —H. In embodiments of the invention wherein the compound is linked to a solid support $R_6$ may be a linker covalently linked to a solid support. The linker and the solid support may be any of the linker or solid support described herein below. Preferably the linker is cleavable, and it is preferred that $R_6$ is —H after cleavage of the linker.

In one embodiment of the invention $R_6$ and X together forms an aliphatic ring including the N-atom to which $R_6$ is attached. Accordingly, said aliphatic ring will comprise at least one N. It is preferred that the aliphatic ring is 4 to 8 membered, more preferably 5 to 6 membered. More preferably, the ring comprises only one N. In a very preferred embodiment the ring is selected from the group consisting of pyrrolidine and piperidine. The phenyl group may be linked to any position of the aliphatic ring, preferably to position 5 of pyrrolidine or to position 4 of piperidine. The aliphatic ring may be substituted, preferably with an amide, more preferably with —$CONH_2$.

$R_7$ and $R_9$ may together form a 4 to 6 membered ring or 6 to 14 membered fused ring system, preferably an aliphatic ring or ring system. The ring may for example by a 5 membered ring, whereas the ring system for example may consist of two 6 membered fused rings. The ring or ring system may comprise heteroatoms. Because $R_9$ is linked to N, then the rings will at least comprise N. It is also possible that the rings comprises additional heteroatoms, such as additional N, S or O, preferably, however, the ring only comprises one heteroatom, i.e. N. The rings may optionally be substituted, for example with phenyl, $NHR_{16}$, $NR_{17}R_{18}$ or —NH—CO—$R_{16}$, wherein $R_{16}$ may be selected from the group consisting of 3 to 6 membered aliphatic or aromatic rings, halide, $C_{1-6}$ linear or branched alkyl and $C_{1-6}$ alkyl substituted with any of the aforementioned, preferably $R_{16}$ may be benzyl, $R_{17}$ and $R_{18}$ may individually be selected from the group consisting of 3 to 6 membered aliphatic or aromatic rings, halide, $C_{1-6}$ linear or branched alkyl and $C_{1-6}$ alkyl substituted with any of the aforementioned.

In one preferred embodiment $R_7$ and $R_9$ together forms 5 membered aliphatic ring comprising N, preferably a ring of the formulae:

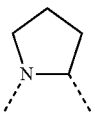

Said ring may optionally be substituted with any of the substituents described herein above. In a preferred embodiment $R_7$ and $R_9$ together forms:

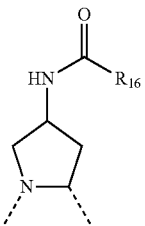

$R_{16}$ may for example be selected from the group consisting of 3 to 6 membered aliphatic or aromatic rings, halide, $C_{1-6}$ linear or branched alkyl and $C_{1-6}$ alkyl substituted with any of the aforementioned. Thus $R_{16}$ may for example be a $C_3$ aliphatic ring, a $C_5$ aliphatic ring, a $C_6$ aliphatic ring, a 5 membered aromatic ring comprising 0, benzyl, phenyl substituted with fluoro, $C_1$ alkyl, $C_3$ branched alkyl, $C_4$ branched alkyl or $C_5$ branched alkyl.

In another preferred embodiment $R_7$ and $R_9$ together forms,

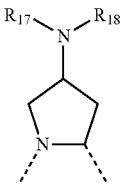

$R_{17}$ and $R_{18}$ may individually be selected from the group consisting of 3 to 6 membered aliphatic or aromatic rings, halide, $C_{1-6}$ linear or branched alkyl and $C_{1-6}$ alkyl substituted with any of the aforementioned. Thus $R_{17}$ may for example be —H and $R_{18}$ may be $CH_2(C_6H_{11})$.

In another embodiment $R_7$ and $R_9$ together forms a 6 membered aliphatic ring comprising N. For example $R_7$ and $R_9$ together forms a 6 membered aliphatic ring comprising only one heteroatom, wherein the heteroatom preferably is an N. Said 6 membered ring may be unsubstituted.

In yet another embodiment $R_7$ and $R_9$ together forms a 4 membered aliphatic ring comprising N. For example $R_7$ and $R_9$ together forms a 4 membered aliphatic ring comprising only one heteroatom, wherein the heteroatom preferably is an N. Said 4 membered ring may be unsubstituted.

In a still further embodiment $R_7$ and $R_9$ together forms a fused ring system of two 6 membered rings, preferably the ring system is a 10 membered ring system. The ring comprises N. For example $R_7$ and $R_9$ together forms a 10 membered ring system comprising only one heteroatom, wherein the heteroatom preferably is an N. Thus said fused ring system may be tetrahydroquinoline. Said 6 membered ring may be unsubstituted comprising N, such as only one heteroatom, which is an N. Said 6 membered ring may be unsubstituted.

In a preferred embodiment of the invention $R_7$ and $R_9$ together forms:

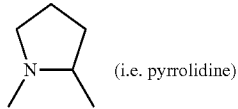
(i.e. pyrrolidine)

wherein the pyrrolidine is substituted phenyl or a secondary amine, preferably with phenyl or —NH—$CH_2$—($C_{4-10}$ aromatic or aliphatic ring system), more preferably with phenyl or —NH—$CH_2$-cyclohexyl. It is preferred that the pyrrolidine is substituted at the 4 or 5 position, more preferably if the pyrrolidine is substituted with phenyl it is preferred that it is on the 5 position and if the pyrrolidine is substituted with a secondary amine it is preferred that it is on the 4 position. at the 5 position with phenyl.

Optionally, Y may also form part of the 4 to 6 membered ring or 6 to 14 membered fused ring system formed by $R_7$ and $R_9$. Y may be $(CH_2)_n$, wherein n is an integer in the range of 0 to 2, such as 0, for example 1, such as 2, preferably 0.

In a preferred embodiment of the invention $R_7$, Y and $R_9$ together forms a $C_5N$ aliphatic ring (i.e. a 6 membered aliphatic ring), wherein the ring is preferably not substituted.

In embodiments of the invention wherein $R_7$ and $R_9$ together form a ring or ring system, then $R_8$ preferably is —H or phenyl. In particular when Y is $(CH_2)_2$, then $R_8$ may be phenyl. Otherwise $R_8$ preferably is —H.

In embodiments of the invention wherein $R_7$ and $R_9$ do not form a ring or a ring system then $R_7$ and $R_8$ together may form a 4 to 6 membered ring, which optionally may be substituted with $C_{1-6}$ alkyl, halid, $C_{1-6}$ alkyl halid, OH, $OR_{16}$, $NH_2$ or $NHR_{16}$ or $NR_{17}R_{18}$. Preferably $R_7$ and $R_8$ together may form a cyclopentyl or cyclohexyl ring. $R_{16}$, $R_{17}$ and $R_{18}$ may be as described above. In this embodiment $R_9$ is preferably —H.

In a preferred embodiment of the invention $R_7$ and $R_8$ together forms a $C_6$ aliphatic ring.

$R_7$ and $R_8$ may also individually be selected from the group consisting of —H and 3 to 6 membered aliphatic and aromatic rings. Preferably at least one, more preferably exactly one of $R_7$ or $R_8$ is a 3 to 6 membered aliphatic or aromatic ring, such as an heteroaromatic ring. The heteroaromatic ring may preferably comprise the heteroatom S, more preferably only one S. Thus for example $R_8$ may be phenyl or a $C_5$ aliphatic ring. In this embodiment of the invention $R_9$ may be —H, but it is also comprised within the invention that $R_7$ and $R_9$ may form a ring or a ring system and $R_8$ comprises a ring.

In a preferred embodiment of the invention $R_7$ is selected from the group consisting of —$CH_2$-phenyl, —$CH_2$—$CH_2$—$CONH_2$ and —$CH_2$-thienyl.

$R_{10}$ and $R_{11}$ may individually be selected from the group consisting of $C_{1-6}$ linear and branched alkyl, $C_{1-6}$ alcohol, $C_{1-6}$ alkoxy, 3 to 6 membered aliphatic and aromatic rings, $C_{2-6}$ carboxylic acids, $C_{2-6}$ esters, $C_{2-6}$ carbonyl, $C_{1-6}$ amides, halide, $C_{2-6}$ ether or any of the aforementioned substituted with $C_{3-6}$ branched alkyl, halide, 3 to 6 membered aliphatic or aromatic rings. In one preferred embodiment at least one of $R_{10}$ and $R_{11}$ is a 6 membered aliphatic ring. $R_{10}$ and $R_{11}$ may also individually be —H, it is however preferred that only one of $R_{10}$ and $R_{11}$ is —H. It is preferred within the present invention that neither $R_{10}$ nor $R_{11}$ are isopropyl or tertbutyl. In this embodiment of the invention it is preferred that $R_{12}$ is —H.

In embodiments of the invention, wherein $R_{10}$ is isopropyl or tertbutyl, then it is preferred that X is $C_{1-5}$ alkyl substituted with an amide, preferably said amide is a $C_{0-5}$ amide, more preferably —$C(O)NH_2$. In a preferred embodiment X is selected from the group consisting of —$CH(CONH_2)$—, —$CH(CONH_2)$—$CH_2$—, $CH(CONH_2)$—$CH_2$—$CH_2$— and —CH—$CH_2(CONH_2)$, more X is selected from the group consisting of —$CH(CONH_2)$—$CH_2$— and —CH—$CH_2(CONH_2)$, even more preferably X is —$CH(CONH_2)$—$CH_2$.

In one embodiment $R_{10}$ may be of the formulae:

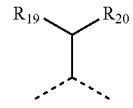

$R_{19}$ may be —H or alkyl, preferably —H or $CH_3$ and $R_{20}$ may be $C_{2-6}$, preferably $C_{2-3}$ linear or branched alkyl, —$CH_3$, a $C_6$ aliphatic ring, phenyl, phenyl halide, OH, a 5 membered heteroaromatic ring comprising S or N, or $(CH_2)_n(CO)Z$, wherein n is 0, 1 to 2 and Z is OH, $NH_2$, $NHR_{23}$ or $NR_{23}R_{24}$. $R_{23}$ and $R_{24}$ may individually be selected from the group consisting of —H and $C_{1-6}$ alkyl optionally substituted with halide, hydroxyl or amino. Said heteroaromatic ring may for example be a $C_3N_2$ heteroaromatic ring or a $C_4S$ heteroaromatic ring.

In another embodiment $R_{10}$ is a $C_5$ aliphatic ring.

In a preferred embodiment of the invention $R_{10}$ is selected from the group consisting of a $C_6$ aliphatic ring and substituents of the formulae

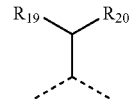

wherein $R_{20}$ is selected from the group consisting of —$CH_2COOH$, —$CONH_2$, —CH—$(CH_3)_2$, —$CH_2CH_3$, —COOH and $CH_3$ and
$R_{19}$ is —$CH_3$ when $R_{20}$ is —$CH_2CH_3$, —$CH_3$ and $R_{19}$ is otherwise —H.

It is also comprised within the invention that $R_{10}$ and $R_{11}$ together forms a 4 to 6 membered ring, such as a $C_5$ or $C_6$ aliphatic ring. In this embodiment it is preferred that $R_{12}$ is —H.

It is also comprised within the invention that $R_{10}$ and $R_{12}$ together may form a 4 to 6 membered ring, such as a 4 membered ring comprising N. In this embodiment $R_{11}$ is preferably —H.

In a preferred embodiment of the invention $R_{11}$ is —H.

$R_{12}$ is preferably —H.

$R_{13}$, $R_{14}$ and $R_{15}$ may individually be selected from the group consisting of $C_{1-6}$ linear and branched alkyl, $C_{1-6}$ alkoxy, 3 to 6 membered aliphatic and aromatic rings, $C_{2-6}$ esters, halide, $C_{1-6}$ amide, amine, $C_{2-6}$ ether or any of the aforementioned substituted with $C_{3-6}$ branched alkyl, halide or 3 to 6 membered aliphatic or aromatic rings. $R_{13}$ may for example be —NH—($C_{1-5}$-alkyl), —NHCH$_3$, $(CH_2)_n NH_2$, wherein n is 0 or 1, —H or —$C_1$, $R_{14}$ may for example be —H, NH$_2$, CH$_3$, CH$_2$CH$_3$, CH$_2$—OH, isobutyl, sec-butyl, isopropyl, cyclopropyl, CH(CH$_3$)—OH or CH$_2$-tertbutyl and $R_{15}$ may for example be —H or CH$_3$.

In a preferred embodiment of the invention $R_{13}$ is an amine, such as a primary or secondary amine, preferably $R_{13}$ is selected from the group consisting of —NH—CH$_3$ and —NH$_2$.

In a preferred $R_{14}$ is $C_{1-2}$ alkyl, which is not substituted or substituted with —OH, preferably $R_{14}$ is selected from the group consisting of —CH$_3$, CH$_2$CH$_3$, —CH(CH$_3$)OH and CH$_2$OH.

It is also comprised within the invention that $R_{13}$ and $R_{14}$ together may form a 4 to 6 membered ring, such as a 4 to 5 membered ring comprising N. In this embodiment $R_{15}$ is preferably —H.

In a preferred embodiment of the invention $R_{13}$ and $R_{14}$ together forms a $C_3N$ aliphatic ring (i.e. a 4 membered ring), which preferably is not substituted.

In a preferred embodiment $R_{15}$ is selected from the group consisting of —H and —CH$_3$.

In one embodiment of the invention $R_{23}$ is cycloalkyl, preferably $C_{4-10}$ cycloalkyl, more preferably a $C_{5-6}$ cycloalkyl. In one embodiment the cycloalkyl is preferably unsubstituted, more preferably the cycloalkyl may be unsubstituted cyclohexyl. In another embodiment the cycloalkyl is substituted with an amide, preferably with —$(CH_2)_n CONH_2$, wherein n is an integer in the range of 0 to 5, preferably in the range of 0 to 1, more preferably 0. $R_{23}$ may in one very preferred embodiment be $C_5$ to $C_6$ cycloalkyl substituted with —CONH$_2$.

In embodiments of the invention wherein $R_{23}$ is cycloalkyl substituted with amide, it is preferred that X is $(CH_2)_n$, wherein n is 0 (i.e. X is absent). In all other embodiments it is preferred that X is $C_{1-5}$ alkyl or alkyl substituted with amide.

In one preferred embodiment of the invention X is absent (i.e. X is —$(CH_2)_n$, wherein n is 0) and $R_{23}$ is cyclopentyl substituted with —CONH$_2$, preferably at the same carbon atom as the position where $R_{23}$ is linked to N.

In one embodiment the invention relates to compounds of the general structure

AA$_4$-AA$_3$-AA$_2$-AA$_1$, wherein each of AA$_1$, AA$_2$, AA$_3$ and AA$_4$ are amino acids linked by peptide bonds. The amino acids may be naturally occurring or not naturally occurring amino acids. AA$_1$ is preferably N-terminal.

In a preferred embodiment AA$_1$, AA$_2$, AA$_3$ and AA$_4$ are selected as follows:

Preferably AA$_1$ is selected from the group consisting of amino acids shown in Table 6, more preferably AA$_1$ is selected from the group consisting of entries 12, 13, 14, 19 and 20 of Table 6, even more preferably AA$_1$ is entry 14 of Table 6.

Preferably AA$_2$ is selected from the group consisting of the amino acids shown in Table 7, more preferably AA$_2$ is selected from the group consisting of entries 3 and 17 of Table 7, more preferably AA$_2$ is entry 17 of Table 7.

Preferably AA$_3$ is selected from the group consisting of amino acids shown in Table 8, more preferably AA$_3$ is selected from the group consisting of entries 1 and 8 of Table 8, even more preferably AA$_3$ is entry 1 of Table 8.

Preferably AA$_4$ is selected from the group consisting of amino acids shown in Table 9, more preferably AA$_4$ is selected from the group consisting of entries 4, 8, 9 and 10 of Table 9, even more preferably AA$_4$ is entry 8 of Table 9.

The compounds may optionally be linked to a solid support, for example AA$_1$ may be linked to a solid support via a linker, such as a cleavable linker, for example any of the cleavable linkers mentioned herein below. In one embodiment the linker may be the Holmes linker. Preferably AA$_1$ comprises an amide group to which the linker is linked. It is preferred that a free amide is generated following cleavage of the cleavable linker. Thus AA$_1$ preferably comprises a free amide group or an amide group covalently linked to a linker, such as a cleavable linker.

One preferred compound according to the invention has the structure

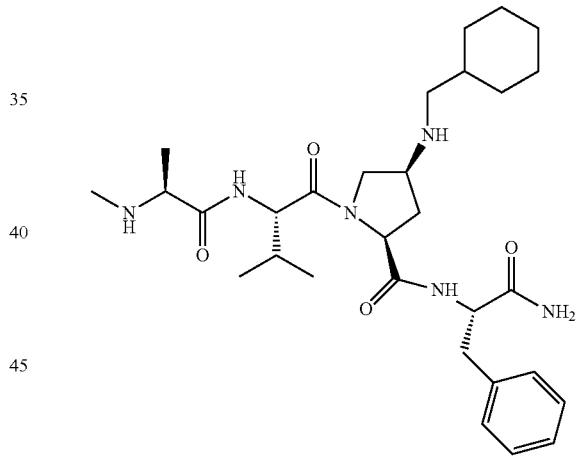

Examples of Preferred Compounds

In one preferred embodiment the present invention relates to compounds of the general structure

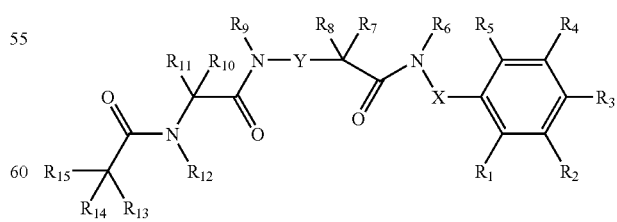

wherein $R_1$, $R_2$, $R_3$, $R_4$ and $R_5$ individually is selected from the group consisting of —H, $C_{1-6}$ alkoxy and phenyl, more preferably from the group consisting of —H, methoxy and phenyl; and X is $C_{1-5}$ alkyl substituted with an amide, such as an $C_{0-5}$ amide, wherein $C_{0-5}$ amides are substituents of the formulae $(CH_2)_n$—$CONH_2$; and $R_6$ is —H; and $R_7$ is selected from the group consisting of $C_{1-2}$ alkyl substituted with —$CONH_2$, phenyl or thienyl, preferably $R_7$ is selected from the group consisting of —$CH_2$-phenyl, —$CH_2$—$CH_2$—$CONH_2$, —$CH_2$-thienyl; or $R_7$ and $R_9$ together forms:

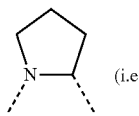

(i.e. pyrrolidine), wherein the pyrrolidine may be substituted with phenyl or a secondary amine, preferably with phenyl or —NH—$CH_2$— ($C_{4-10}$ aromatic or aliphatic ring system), more preferably with phenyl or —NH—$CH_2$-cyclohexyl. It is preferred that the pyrrolidine is substituted at the 4 or 5 position, more preferably if the pyrrolidine is substituted with phenyl it is preferred that it is on the 5 position and if the pyrrolidine is substituted with a secondary amine it is preferred that it is on the 4 position.

$R_7$, Y and $R_9$ together forms a 6 membered $C_5N$ aliphatic ring (i.e. piperidine), wherein $R_9$ is directly attached to the N of the piperidine and wherein the ring is preferably not substituted (except for with $R_8$), and preferably $R_8$ is directly attached to the $C_4$ of the piperidine; or $R_7$ and $R_8$ together forms a $C_{4-6}$ aliphatic ring, preferably a $C_6$ aliphatic ring; and $R_8$ either forms a ring with $R_7$ as described above or $R_8$ is selected from the group consisting of phenyl and —H, preferably $R_8$ is phenyl when $R_7$, Y and $R_9$ forms a piperidine and otherwise preferably $R_8$ is —H; and $R_9$ either forms a ring with $R_7$ and optionally Y as described above or is $R_9$ is —H; and.

Y either forms a ring with $R_7$ and $R_9$ as described above or Y is absent (i.e. Y is $(CH_2)_n$, wherein n is 0); and $R_{10}$ is selected from the group consisting of a $C_6$ aliphatic ring and substituents of the formulae

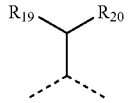

wherein $R_{20}$ is selected from the group consisting of —COOH, $CONH_2$ and $C_{1-3}$ linear or branched alkyl optionally substituted with —COOH or $CONH_2$ and $R_{19}$ is $CH_3$ or —H; and $R_{11}$ is —H; and $R_{12}$ is —H; and $R_{13}$ and $R_{14}$ together forms a 4 to 6 membered aliphatic ring optionally comprising N; or $R_{13}$ is an amine, such as a primary or secondary amine; and $R_{14}$ forms a ring with $R_{13}$ as described above or $R_{14}$ is $C_{1-3}$ linear or branched alkyl, which optionally is substituted with —OH; and $R_{15}$ is selected from the group consisting of —H and —$CH_3$.

Preferably at least 1, more preferably at least 2, even more preferably at least 3 of $R_1$, $R_2$, $R_3$, $R_4$ and $R_5$ are —H.

Even more preferably, $R_1$, $R_4$ and $R_5$ are —H; and $R_2$ is selected from the group consisting of —H and $C_{1-6}$ alkoxy, more preferably from the group consisting of —H and methoxy; and $R_3$ is selected from the group consisting of —H, $C_{1-6}$ alkoxy, and phenyl, more preferably from the group consisting of —H, methoxy and phenyl.

Preferably, X is $C_{1-15}$ alkyl substituted with —$CONH_2$ or $(CH_2)$—$CONH_2$, more preferably X is selected from the group consisting of —CH($CONH_2$)—$CH_2$— and —CH—$CH_2(CONH_2)$, wherein the CH group is directly linked to N and the phenyl group, Preferably, $R_{20}$ is selected from the group consisting of —$CH_2COOH$, —$CONH_2$, —CH—$(CH_3)_2$, —$CH_2CH_3$, —COOH and $CH_3$. It is furthermore preferred that $R_{19}$. is —$CH_3$ when $R_{20}$ is —$CH_2CH_3$ or —$CH_3$ and that $R_{19}$ is otherwise —H.

If $R_{13}$ and $R_{14}$ together forms an aliphatic ring, it is preferred that the ring comprises N, more preferably that it consists of 3 to 5 C and one N, more preferably that it consists of 3 C and one N. It is preferred that the ring is not substituted Otherwise it is preferred that $R_{13}$ is selected from the group consisting of —NH—$C_{1-3}$-alkyl and $C_{0-3}$-alkyl-$NH_2$, more preferably $R_{13}$ is selected from the group consisting of —NH—$CH_3$ and —$NH_2$. In a preferred embodiment $R_{13}$ is —$NH_2$; and $R_{14}$ is $C_{1-2}$ alkyl optionally substituted with —OH, preferably $R_{14}$ is selected from the group consisting of —$CH_3$, $CH_2CH_3$, —CH($CH_3$)OH and —$CH_2OH$.

It is preferred that $R_{15}$ is —$CH_3$ only when $R_{14}$ is —$CH_3$. When $R_{14}$ is not —$CH_3$ it is preferred that $R_{15}$ is —H. When $R_{14}$ is —$CH_3$, then $R_{15}$ is preferably selected from the group consisting of —H and —$CH_3$.

Examples of preferred compounds according to the invention are given in FIG. 2.

In one embodiment the invention relates to compounds of the general structure:

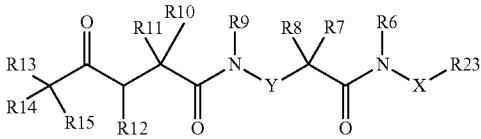

wherein $R_6$ is —H; and $R_7$ is —$(CH_2)_n$—$CONH_2$, wherein n is an integer in the range of 0 to 5, preferably $R_7$ is —$CH_2$—$CH_2$—$CONH_2$ or $R_7$ and $R_9$ together forms a pyrrolidine. Preferably said pyrrolidine is substituted, more preferably with —NH—$CH_2$—($C_{4-10}$ aromatic or aliphatic ring system), more preferably with —NH—$CH_2$-cyclohexyl. It is preferred that the pyrrolidine is substituted at the 4 position; and $R_8$ is H; and $R_9$ forms a ring with $R_7$ as described above or $R_9$ is —H; and $R_{10}$ is $C_{1-5}$ linear or branched alkyl optionally substituted with —$CONH_2$. Thus, $R_{10}$ may in one embodiment preferably be $C_{3-5}$ linear or branched alkyl, more preferably $R_{10}$ is branched butyl, yet more preferably $R_{10}$ is —CH($CH_3$) $CH_2CH_3$ or —$CH_2CH(CH_3)_2$. In another embodiment $R_{10}$ is preferably $CH_2CONH_2$; and $R_{11}$ is —H; and $R_{12}$ is —H; and $R_{13}$ and $R_{14}$ together form a 4 to 6 membered ring, such as a 4 to 5 membered ring comprising N, more preferably a $C_3N$ aliphatic ring (i.e. a 4 membered ring), said ring preferably not being substituted; and $R_{15}$ is H; and
$R_{23}$ is $C_{4-10}$ cycloalkyl, more preferably a $C_{5-6}$ cycloalkyl, even more preferably the cycloalkyl is substituted with an amide, preferably with —$(CH_2)_n CONH_2$, wherein n is an integer in the range of 0 to 5, preferably in the range of 0 to 1, more preferably 0, yet more preferably $R_{23}$ $C_5$ to $C_6$ cycloalkyl substituted with —$CONH_2$; and
X and Y are absent (i.e. X and Y are $(CH_2)_n$, wherein n is 0).

Examples of preferred compounds according to this embodiment are compounds 4, 5 and 6 of FIG. 2.

In one very preferred embodiment the invention relates to compounds as described above, wherein exactly one of $R_1$, $R_2$, $R_3$, $R_4$ and $R_5$ are phenyl, whereas the others are —H, more preferably $R_3$ is phenyl. Such compounds may preferably of the formulae

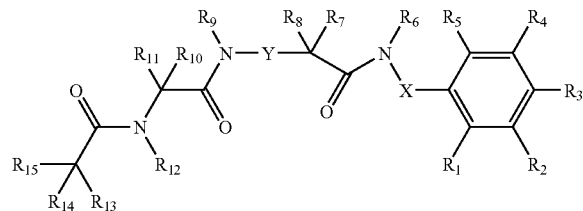

wherein one of $R_1$, $R_2$, $R_3$, $R_4$ and $R_5$ are phenyl, whereas the others are —H, more preferably $R_3$ is phenyl; and
$R_6$ is —H; and
$R_7$ and $R_9$ together forms:

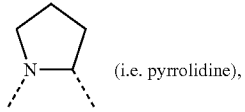
(i.e. pyrrolidine), wherein the pyrrolidine is substituted with phenyl, more preferrably the pyrrolidine is substituted at the 4 or 5 position, even more preferably the pyrrolidine is substituted on the 5 position with phenyl; or
$R_7$, Y and $R_9$ together forms a 6 membered $C_5N$ aliphatic ring (i.e. piperidine), wherein $R_9$ is directly attached to the N of the piperidine and preferably said piperidine is only substituted with $R_8$, more preferably $R_8$ is directly attached to the $C_4$ of the piperidine; and
$R_8$ is —H or phenyl, preferably $R_8$ is —H when $R_7$ and $R_9$ together forms a pyrrolidine, whereas $R_8$ preferably is phenyl when $R_7$, Y and $R_9$ together forms a piperidine; and
$R_9$ either forms a ring with $R_7$ as described above; and
$R_{10}$ is a $C_{3-10}$ aliphatic ring, preferably a $C_{3-6}$ aliphatic ring, more preferably a $C_{5-6}$ aliphatic ring, even more preferably cyclohexyl; and
$R_{11}$ is —H; and
$R_{12}$ is —H; and
$R_{13}$ is —NH—($C_{1-5}$-alkyl) or —$NH_2$, preferably —$NHCH_3$ or —$NH_2$, more preferably —$NH_2$; and
$R_{14}$ is $C_{1-5}$ linear or branched alkyl, preferably methyl or ethyl; and
$R_{15}$ is $C_{1-5}$ linear or branched alkyl or —H, preferably methyl or —H; more preferably when $R_{14}$ is not methyl, $R_{15}$ is —H, and when $R_{14}$ is methyl, then $R_{15}$ is methyl or —H; and
X is $C_{1-5}$ alkyl substituted with an amide, such as with an amide of the formulae —$(CH_2)_n$—$CONH_2$, wherein n is 0 to 5, preferably X is —CH—$CH_2CONH_2$ wherein the CH group is linked to N and the phenyl group; and
Y either forms a ring with $R_7$ and $R_9$ as described above or Y is absent (i.e. Y is $(CH_2)_n$, wherein n is 0) and wherein Y preferably is absent if Y does not form a piperidine with $R_7$ and $R_9$.

Preferred compounds according to this embodiment include compounds 9, 10, 11 and 12 of FIG. 2.

In another preferred embodiment the invention relates to compounds of the formulae

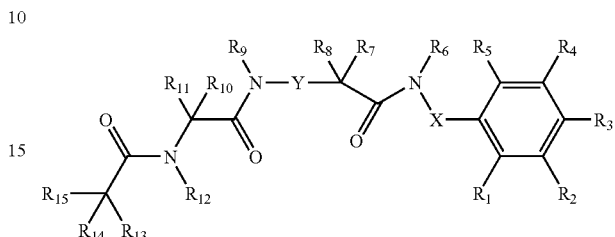

wherein one of $R_1$, $R_2$, $R_3$, $R_4$, $R_5$ and $R_6$ are —H; and
$R_7$ and $R_9$ together forms:

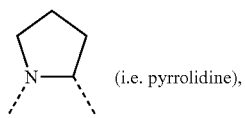
(i.e. pyrrolidine), wherein the pyrrolidine is substituted with a secondary amine, preferably with —NH—$CH_2$—($C_{4-10}$ aromatic or aliphatic ring system), more preferably with —NH—$CH_2$-cyclohexyl. It is preferred that the pyrrolidine is substituted at the 4 or 5 position, more preferably on the 4 position; and
$R_8$ and $R_9$ are —H; and
$R_{10}$ is a $C_{1-5}$ linear or branched alkyl, preferably a $C_{3-4}$ linear or branched alkyl, more preferably a $C_3$ linear or branched alkyl, even more preferably —$CH(CH_3)_2$; and
$R_{11}$ is —H; and
$R_{12}$ is —H; and
$R_{13}$ is —NH—($C_{1-5}$-alkyl) or —$NH_2$, preferably —NH—($C_{1-3}$-alkyl), more preferably —$NHCH_3$; and
$R_{14}$ is $C_{1-5}$ linear or branched alkyl, preferably methyl or ethyl, more preferably methyl; and
$R_{15}$ is —H; and
X is $C_{1-5}$ alkyl substituted with an amide, such as with an amide of the formulae —$(CH_2)_n$—$CONH_2$,
wherein n is 0 to 5, preferably X is —CH($CONH_2$)—$CH_2$—; and
Y is absent (i.e. Y is $(CH_2)_n$, wherein n is 0).

A preferred compound according to this embodiment is 2CX4.401 (Example 7).

Production of Compounds

The compounds according to the invention may be prepared by any useful method known to the skilled person.

In one embodiment of the invention, the compound is immobilised on a solid support, such as a resin bead. The resin bead may be any of the resin beads described herein below.

Typically the resin bead comprises or is covalently coupled to a linker comprising a reactive group upon which the compound may be directly synthesised. Useful linkers are described herein below.

In one embodiment the linker comprises an aldehyde or a masked aldehyde, which may be transformed into an aldehyde. Said aldehyde may be made to react by reductive amination with the amino group of a compound of formulae:

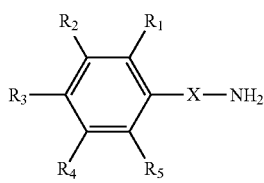

such as a phenylethylamine, for example any of the phenylethylamines disclosed in Table 1.

Following reductive amination, an amino acid may be added via the carboxyl group for example by a bis(trichloromethyl)carbonate (BTC) mediated coupling. Standard coupling conditions like TBTU/NEM or EDC/DIPEA may also be employed but tend to be less efficient due to the secondary nature of the coupling amine linked to the solid phase. Preferably, the amino group of said amino acid is protected by a protective group such as Fmoc or another protective group, for example Boc, $N_3$ or Alloc. Sidechains may optionally be protected with acid labile protecting groups such as t-Bu, Trt, Pmc, Boc etc. The amino acid, may be any amino acid comprising $R_7$, $R_8$ and $R_9$ as defined herein above, wherein $R_9$ is directly linked to the amino group. For example the amino acid may be one of the amino acid mentioned in Table 2, wherein side group NHBoc groups optionally may be deprotected and acylated with any of the compounds mentioned in Table 3. Acylation may be performed prior to or after coupling of the amino acid.

As the next step an additional amino acid may be added via the carboxyl group to the amino group of the above mentioned coupled amino acid. If the amino group is protected with a protective group, said protective group may first be removed by conventional methods. Afterwards the second amino acid may be added for example by a TBTU coupling. Preferably, the amino group of the second amino acid is protected by a protective group such as Fmoc or another protective group, for example Boc, $N_3$ or Alloc. Sidechains may optionally be protected with acid labile protecting groups such as t-Bu, Trt, Pmc, Boc etc. Useful amino acid are any amino acid comprising $R_{10}$, $R_{11}$ and $R_{12}$ as defined herein above, wherein $R_{12}$ is directly linked to the amino group, for example the amino acid may be any of the amino acids described in Table 4.

As the next step an additional amino acid or an acyl halide may be added via the carboxyl group to the amino group of the above mentioned coupled amino acid. If the amino group is protected with a protective group, said protective group may first be removed by conventional methods. Afterwards the third amino acid or acyl halide may be added for example by a TBTU coupling. Useful amino acid are any amino acid or acyl halide comprising $R_{13}$, $R_{14}$ and $R_{15}$ as defined herein above, for example any of the compounds described in Table 5.

In another embodiment of the invention a linker, such as a Holmes-type linker is coupled to a resin bead comprising a free —$NH_2$ group by standard methods, such as by standard TBTU coupling. Amino acids may then sequentially be coupled to the linker. Preferably, the amino groups of the amino acids are protected, for example by an Fmoc group. If the amino acids comprise more than one —$NH_2$ group, they are preferably all protected. The amino group used for coupling is preferably protected by Fmoc, whereas the other amino group for example may be protected with Boc.

The first coupling may be reaction of the linker, preferably of the —$NH_2$ group of the linker for example by SPPS TBTU coupling. The first coupling may be with any useful amino acid comprising an X—$R_{23}$ group as defined above, with the proviso that the amide group of X described above may be a carboxylic acid group, which is transformed to an amide only after reaction with the —$NH_2$ of the linker. Preferably, the first coupling is made using any of the amino acids mentioned in Table 6.

The second coupling may be a reaction with the —$NH_2$ of the first amino acid, for example by SPPS TBTU coupling. In the event that the —$NH_2$ group of the first amino acid was protected it should preferably be deprotected before the second coupling. The second amino acid may be any amino acid comprising $R_7$, $R_8$ and $R_9$ as defined herein above, wherein $R_9$ is directly linked to the amino group. For example the amino acid may be one of the amino acid mentioned in Table 7.

The third coupling may be a reaction with the —$NH_2$ of the second amino acid, for example by SPPS TBTU coupling. In the event that the —$NH_2$ group of the second amino acid was protected it should preferably be deprotected before the third coupling. The third amino acid may be any amino acid comprising $R_{10}$, $R_{11}$ and $R_{12}$ as defined herein above, wherein $R_{12}$ is directly linked to the amino group, for example the amino acid may be any of the amino acids described in Table 8.

The fourth coupling may be a reaction with the —$NH_2$ of the third amino acid, for example by SPPS TBTU coupling. In the event that the —$NH_2$ group of the third amino acid was protected it should preferably be deprotected before the third coupling. The forth amino acid may be any amino acid comprising $R_{13}$, $R_{14}$ and $R_{15}$ as defined herein above, for example any of the compounds described in Table 9.

Library

The libraries according to the invention may comprise at least 2, preferably at least 10, more preferably at least 20, such as at least 100, for example at least 1000, such as at least 10,000, for example at least 100,000, such as at least 1,000,000 different test compounds. Preferably, the libraries comprises in the range of 20 to $10^7$, more preferably 50 to 7,000,000, even more preferably 100 to 5,000,000, yet more preferably 250 to 2,000,000 different compounds. In a very preferred embodiment of the present invention the libraries comprises in the range of 1000 to 20,000 or for example in the range of 20,000 to 200,000 different compounds.

In preferred embodiments of the invention the library comprises in the range of 10,000 to 1,000,000 different compounds.

Preferably, the libraries to be used with the present invention are immobilised on resin beads. Said resin beads may be any of the beads described herein below. The libraries comprises at least 2, preferably at least 20, more preferably at least 100, even more preferably at least 1000, yet more preferably at least 10,000, for example at least 100,000, such as at least 1,000,000 resin beads comprising different library members, i.e. different test compounds may be used with the methods according to the invention. Preferably, the in the range of 20 to $10^7$, more preferably 100 to 7,000,000, even more preferably 1000 to 5,000,000, yet more preferably 5000 to 2,000,000, even more preferably 10,000 to 1,000,000 resin beads comprising different library compounds.

In one very preferred embodiment of the invention, each resin bead does not comprise more than one library compound in one or more copies, i.e. each resin bead only comprises one kind of library compound, however said library compound may be present on the resin bead in multiple copies. Such libraries may also be designated one-bead-one-compound libraries. In one embodiment, each resin bead comprises sufficient copies of said compound in order to induce apoptosis in cells attached to said resin bead and in order to analyse the chemical structure of the compound.

The libraries may be prepared by different methods, for example by a split/mix method or by coupling individually a specific compound to a bead. One-bead-one compound libraries offer the advantage that once a resin bead comprising a useful compound has been selected according to the methods described herein, the desired compound may easily be identified (see useful methods herein below).

The libraries may in one preferred embodiment be synthesized directly on resin beads using a split/mix method (vide infra), which gives rise to one-bead-one-compound libraries. Split/mix methods in general comprise the steps of:
1. Providing several pools of resin beads
2. Performing one or more different chemical synthesis steps on each pool of resin beads
3. Mixing pools of resin beads, thereby obtaining a mixed pool.
4. Splitting the mixed pool of resin beads thereby obtaining new pools.
5. Optionally repeating step 1 and 4

Alternatively steps 3 and 4 may be as follows:
3. Splitting said pools to obtain fractions
4. Mixing fractions from different pools, thereby obtaining new pools In another embodiment of the invention the library may be a one-bead-two-compounds library. Each individual resin bead of such a library comprises only one library member in one or more copies. In addition each individual resin bead comprises a second compound, such as a peptide. One-bead-two-compound libraries may for example be prepared by a method involving the steps of:
1. Providing resin beads comprising a plurality of reactive groups
2. Reacting said reactive groups with two chemical moeities comprising different and orthogonal protective groups
3. Deprotecting a subset of the reactive groups by removal of one kind of protective groups
4. Attaching or synthesizing a split/mix library of test compounds to the deprotected reactive group
5. Deprotecting the remaining reactive groups by removal the other kind of protective group
6. Attaching the second compound to the deprotected reactive groups Preferred resin beads are described in the section "resin beads" herein below. The reactive group may be any suitable reactive group, preferably however, the reactive group is either a hydroxyl group, a thiol or a primary amino group. The protective group may be any suitable protective group known to the person skilled in the art, such as acid labile, alkaline labile, fluoride labile, oxidation labile, reduction labile or photolabile protective groups, preferably the protective group is selected from the group consisting of Fmoc, Boc, Alloc and $N_3$. It is preferred that the different protective groups may be removed by different treatment, for example that if one protective group is acid labile, then the other is not acid labile, but instead for example alkaline labile or photo labile. In an preferred embodiment one protective group is Fmoc and the other protective group is Alloc or $N_3$. Step 3 may for example be performed by a split/mix method as described herein above, thereby generating a one-bead-one-compound library. The second compound is preferably a cell adhesion compound.

Resin Beads

The library members or compounds of this invention may be bound to a solid support. Preferred solid supports to be used with the present invention are resin beads (see herein below).

Preferred solid supports useful with the present invention satisfy the criteria of being suitable for organic synthesis. It is thus preferable that the compounds of the invention may be directly synthesised onto the solid support. In some embodiments of the invention it is also preferred that the solid support is suitable for screening procedures, such as "on-bead" screening for compounds capable of inhibiting binding of the Smac protein to Inhibitor of apoptosis (IAP) and/or promoting apoptosis. It may furthermore be preferable that the solid support is suitable for attachment of cells. In addition it is preferred that the resin bead is suitable for "on-bead" identification of library members as described herein below. Preferably, the solid support is a resin bead. The resin bead may be prepared from any suitable material such as polystyrene, polyethylene, polyacrylamide, controlled pore glass or PEG. The resin bead could thus for example be selected from the group consisting of Toyopearl, sepharose, sephadex, CPG, silica, POPOP, PEGA, SPOCC, Expansin, Tentagel, Argogel, Polystyrene, Jandagel, polydimethylacrylamide resin, Polyacrylamide resin, kieselgur supported resins and polystyrene supported resins.

Hydrophilic supports are preferred. Examples of preferred hydrophilic resin beads includes TentaGel (commercially available from Rapp polymere, Tubingen, Germany), Argo-Gel (commercially available from Argonaut Technologies Inc., San Carlos, Calif.), PEGA (commercially available from VersaMatrix, Copenhagen), POEPOP (Renil et al., 1996, Tetrahedron Lett., 37: 6185-88; available from Versamatrix, Copenhagen, Denmark) and SPOCC (Rademann et al, 1999, J. Am. Chem. Soc., 121: 5459-66; available from Versamatrix, Copenhagen, Denmark). Examples of on-bead screening attempts are described in the following references: Chen et al., 1996, Methods Enzymol., 267: 211-19; Leon et al., 1998, Bioorg. Med. Chem. Lett., 8: 2997-3002; St. Hilaire et al., 1999, J. Comb. Chem., 1: 509-23; Smith et al., 1999, J. Comb. Chem., 1: 326-32; Graven et al., 2001, J. Comb. Chem. 3: 441-52; Park et al., 2002, Lett. Peptide Sci., 8: 171-78). TentaGel and ArgoGel are made up of polyethylene glycol chains grafted on to a polystyrene core. However, use of these supports in biological screening is limited by a size restriction, and by denaturation of certain proteins, particularly enzymes.

Preferred resin beads according to the present invention are resin beads, useful for on-bead library synthesis, screening and identification of ligand/protein. Hence, preferred resins according to the present invention are resin comprising polyethylene glycol. More preferably, the resin is PolyEthyleneGlycol Acrylamide copolymer (PEGA), Super Permeable Organic Combinatorial Chemistry (SPOCC) resin or PolyOxyEthylene-PolyOxyPropylene (POEPOP) resin. Another preferred resin comprises a crosslinked polyacrylamide resin.

PEGA (PolyEthyleneGlycol Acrylamide copolymer; Meldal M., 1992, Tetrahedron Lett., 33: 3077-80), POEPOP (PolyOxyEthylene-PolyOxyPropylene resin; Renil et al., 1996, Tetrahedron Lett., 37: 6185-88) and SPOCC (Super Permeable Organic Combinatorial Chemistry resin; Rademann et al, 1999, J. Am. Chem. Soc., 121: 5459-66) resins are made primarily of polyethylene glycol and swell well in organic as well as aqueous solvents. Because they have very reduced or no non-specific binding, PEGA and SPOCC resins have been effectively used in the screening of myriad proteins including enzymes of different classes. Furthermore, these resins are available in different pore sizes and can allow large proteins to enter while retaining activity.

In some embodiments of the invention it is preferred that cells are capable of adhering to the resin beads. Accordingly, the resin beads may comprise an adhesion compound enabling or facilitating cell adhesion. Said adhesion compound may be directly attached to the resin bead or it may be attached via a linker, such as a cleavable linker. Any cell adhesion compound known to the person skilled in the art may be used with the present invention. It is frequently an advantage if the cell adhesion compound comprises at least one positively charged moiety at neutral pH, more preferably the cell adhesion compound has a positive overall netcharge at neutral pH.

In one preferred embodiment of the invention the cell adhesion compound comprises a peptide or a polypeptide, more preferably the cell adhesion compound consists of a peptide, wherein said peptide preferably consists of in the range of 3 to 100, preferably in the range of 3 to 75, more preferably in the range of 3 to 50, even more preferably in the range of 3 to 30, yet more preferably in the range of 3 to 25, even more preferably in the range of 3 to 20, yet more preferably in the range of 3 to 15, such as in the range of 4 to 10 amino acid. Suitable adhesion compounds are described in Danish patent application PA 2004 00821 and includes for example any of the peptides described in Table 2 of that application, which is hereby incorporated by reference in its entirety.

The adhesion compound, such as adhesion peptide may be coupled to the resin bead by any useful method, for example by synthesising the peptide directly onto the resin beads for example using a standard Fmoc-protocol for peptide synthesis. Other protective groups may be used instead of Fmoc, for example Boc, $N_3$ or Alloc. The peptide may also be synthesised by anchoring an Fmoc amino acid to a hydroxyl functionalised resin bead, such as a hydroxymethylbenzoic acid (HMBA) derivatised PEGA resin followed by peptide assembly using standard Fmoc technology as described in B. Blankemeyer-Menge, M. Nimtz, and R. Frank, An Efficient method for ancoring Fmoc-amino acids to hydroxyl-functionalised solid supports. Tetrahedron Lett. 31:1701-1704, 1990 and A. Dryland and R. C. Sheppard. Peptide synthesis. Part 11. A system for continuous flow solid phase peptide synthesis using fluorenylmethoxycarbonyl-amino acid pentafluorophenyl esters. *Tetrahedron* 44(3):859-876, 1988. Preferably a branching amino acid is inserted before the cell adhesion peptide in order to increase the number of cell adhesion molecules. Sidechains may be protected with acid labile protecting groups such as t-Bu, Trt, Pmc, Boc etc. which may be cleaved off by conventional methods. The direct bound peptide may for example be cleaved off the resin using alkaline conditions or hydrazine and the structure may be determined e.g. by on bead Edman Degradation. The HMBA-linked peptide may be cleaved under mild alkaline condition.

Cleavable Linker

The compounds according to the invention may be linked to the resin beads by a linker, such as by a cleavable linker. The cleavable linker may be any chemical moiety which may be used to attach any molecule to a solid support either covalently or via complex formation, and thereafter release said molecule by the action of either acid, base, electrophiles, nucleophiles, oxidative agents, reductive agents, metals or light. Preferably, the cleavable linker attaches the library member to the solid support covalently. Depending on the nature of the cleavable linker, a person skilled in the art will be capable of controlling cleavage of the cleavable linker, so only a proportion of the copies of a library member are released. A comprehensive review describing state of the art for "cleavable linkers" is "Linkers and Cleavage Strategies in Solid-Phase Organic Synthesis and Combinatorial Chemistry", F. Guillier, D. Orain, and M. Bradley, *Chem. Rev.* 2000, 100, 2091-2157. Any of the cleavable linkers described therein may be used with the present invention.

The cleavable linker may be attached to any of the compounds described herein above at any useful position. In one preferred embodiment the cleavable linker will be attached to the X group of the compounds, preferably via the amide group of the X-group.

Examples of useful acid labile linkers include the most commonly used linkers for acidic detachment from a solid support, the Wang and Rink linkers, including peptide esters from Wang linkers, Rink esters and Rink amides. Examples of useful base-labile linkers include Wang and HMBA linkers. In a preferred embodiment the cleavable linker is a light sensitive cleavable linker which, upon the action of light with a given wave length and intensity, may release any active compound from the solid support.

Photo-labile linkers may be o-nitrobenzyl type of linkers (nitrated analogs of the Wang linker), NBA type linkers or Holmes-type linkers.

Example of a Preferred Photo Sensitive Cleavable Linker:

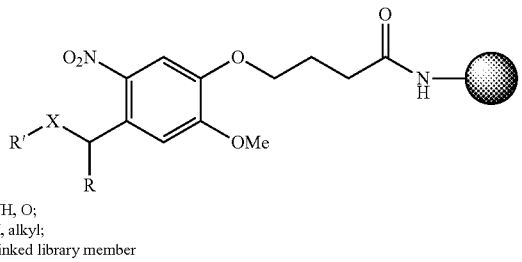

X = NH, O;
R = H, alkyl;
R' = linked library member

Depending on the nature of the cleavable linker, the library member may be released using different methods. For example, if the linker is photo labile, the library member may be released by illumination. The release may be partial. A skilled person will readily be able to identify suitable conditions, including suitable conditions for partial release, which may be useful for cellular assays as well as for release of (optionally remaining) compound for analysis.

In embodiments of the invention wherein both an adhesion compound and a compound according to the invention are linked via cleavable linkers to a resin bead it is preferably that the cleavable linkers are different, preferably they are differentially cleavable.

Compounds Capable of Inducing Apoptosis

Compounds according to the present invention are preferably capable of binding to an inhibitor of apoptosis of the IAP-family, for example XIAP, cIAP1/BIRC2, ML-IAP/BIRC7, DIAP1, DIAP2, OPIAP3, cIAP2, NAIP, Apollon or Survivin or a fragment thereof. The fragment preferably comprises a BIR domain (see Vaux and Silke, 2005, Nature Reviews, 6:287-297).

The compounds according to the present invention are preferably capable of binding to the BIR3 domain of XIAP and/or the BIR domain of ML-IAP, preferably the compound is capable of interrupting binding between Smac and the BIR3 domain of XIAP and/or the BIR domain of ML-IAP. More preferably, the compounds according to the invention are capable of inducing or facilitating apoptosis in living cells, preferably by altering Caspase 3 or 7 activity.

Thus the invention in one embodiment relates to methods of identifying a compound capable of interrupting binding between Smac and a member of the IAP family, preferably XIAP or ML-IAP or a Smac binding fragment thereof, wherein said fragment comprises the BIR-3 domain of XIAP or the BIR domain of ML-IAP, comprising the steps of
a. Providing Smac
b. Providing an IAP, for example XIAP or ML-IAP or a Smac binding fragment thereof
c. Contacting Smac and XIAP or ML-IAP or a Smac binding fragment thereof with a library comprising compounds according to the invention
d. Identifying compounds capable of interrupting binding between Smac and XIAP or ML-IAP or a Smac binding fragment thereof.

The IAP may be any of the above-mentioned IAPs. Smac binding fragments preferably comprises at least one BIR domain. In one embodiment the Smac binding fragment of ML-IAP at least comprises the BIR domain (Matthew C. Franklin et al., *Biochemistry* 2003, 42, 8223-8231). In another embodiment the Smac binding fragment of XIAP at least comprises the BIR3 domain (Wu, G., Chai, J., Suber, T. L., Wu, J.-W., Du, C., Wang, X., and Shi, Y. (2000) *Nature* 408, 1008-1012.)

Binding between Smac and XIAP, ML-IAP or a Smac binding fragment thereof may be identified by any conventional method known to the skilled person. For example, binding may be determined in vitro by a number of different assays. For example either Smac or XIAP, ML-IAP or a Smac binding fragment thereof may be immobilised on a solid support, such as on a resin bead. After incubation with or without the compound of the invention, binding may be detected by detecting whether the other binding partner binds said solid support. This may be performed by directly or indirectly detecting the other binding partner, for example by the aid of a molecule, such as an antibody capable of specifically binding the other binding partner. It is also possible that Smac, XIAP, ML-IAP or a Smac binding fragment thereof is linked to a detectable label, such as a fluorescent label (such as GFP) or a tag. Said tag may for example be one of a pair of specific binding partners, such as epitope/antibody or biotin/streptavidin or avidin. The tag can then be detected with the aid of the binding partner, which preferably is linked to a detectable label.

Detectable labels according to the invention may for example be a fluorescent compound, a radioactive compound, a coloured compound, an enzyme or a heavy metal.

As a reference Smac, XIAP, ML-IAP or a Smac binding fragment may be used. Thus, if Smac is immobilised to a resin bead, then preferred compounds are compounds which at least disrupt binding of XIAP, ML-IAP or a Smac binding fragment thereof to said resin bead to the same extent as non-immobilised Smac. Vice versa, if XIAP, ML-IAP or a Smac binding fragment thereof is immobilised to a resin bead, then preferred compounds are compounds which at least disrupt binding of Smac to said resin bead to the same extent as non-immobilised XIAP, ML-IAP or a Smac binding fragment thereof. Preferred compounds are compounds wherein less than 50%, preferably less than 40%, such as less than 35%, for example less than 30%, such as less than 25%, for example less than 20% compound is required to obtain the same degree of disruption as for the reference compound.

In one example Smac may be linked to biotin and immobilised on resin beads linked to streptavidin. The BIR3 domain of XIAP may be linked to a GST tag and fluorescently labelled antibodies specifically binding to GST may be employed to detect the BIR3 domain. Thus, if a compound is capable of disrupting interaction no or little fluorescence should be associated with the resin beads. Preferred compound are compounds wherein a concentration of less than 100 nM, preferably less than 90 nM, more preferably less than 80 nM, such as less than 70 nM, for example less than 60 nM, such as less than 50 nM of said compounds interrupt interaction to a similar extent as 200 nM Smac.

Other useful assays for determining binding between Smac and XIAP or ML-IAP or a Smac binding fragment thereof may be performed within living cells, such as in any of the cells described herein below. In embodiments where mammalian cells are employed the assays are preferably performed ex vivo. Mammalian cells may be cultivated by any conventional method ex vivo.

In one embodiment of the invention mammalian cells are cultivated directly on resin beads comprising the compounds of the invention. Preferably, such resin beads also comprises an adhesion compound as described herein above. Suitable assays using mammalian cells cultivated on resin beads are described in Danish patent application PA 2004 00821 as well as in PCT application PCT/Dk2005/000347 claiming priority of said Danish patent application (both application are hereby incorporated by reference in their entirety).

Useful assays for determining binding between Smac and XIAP or ML-IAP or a Smac binding fragment thereof in vivo or ex vivo are based on FRET or BRET. Such assays may however also be performed in vitro. In BRET based assays then either between Smac and XIAP or ML-IAP or a Smac binding fragment thereof is linked to a bioluminescent moiety, preferably a bioluminescent protein, such as luciferase and the other binding partner is linked to a fluorescent moiety, such as a fluorescent protein, for example GFP. The bioluminescent moiety should preferably be able to directly or indirectly generate light of a wavelength capable of exciting the fluorescent moiety. The skilled person will readily be able to select useful bioluminescent moieties and fluorescent moieties. Such an assay may be performed by introducing into a cell a nucleic acid encoding a chimeric protein comprising either Smac or XIAP, ML-IAP or a Smac binding fragment thereof and a bioluminescent protein and another nucleic acid encoding another chimeric protein comprising the other binding partner and a fluorescent protein. Direct interaction between the proteins can after expression of the two chimeric proteins be detected through occurrence of BRET (Bioluminescence Resonance Energy Transfer). In one embodiment, BRET2 technology may be used which is based on energy transfer between a bioluminescent donor (a *Renilla* luciferase (Rluc) fusion protein) and a fluorescent acceptor (a Green Fluorescent Protein (GFP2) fusion protein). In presence of its substrate DeepBlueC™ (a coelenterazine derivative), Rluc emits blue light (~395 nm). A protein-protein interaction between Rluc and GFP2 chimeric proteins allows energy transfer to GFP2, which reemits green light (510 nm). Expression of Rluc alone, in the presence of the substrate DeepBlueC™, gives an emission spectrum with a peak at 395 nm, whereas when the Rluc and GFP2 chimeric proteins interact, there is efficient energy transfer between Rluc and GFP2 and the 510 nm signal represents a major peak.

In FRET based assays Smac and XIAP or ML-IAP or a Smac binding fragment thereof, respectively, are linked to different fluorescent moieties, preferably a fluorescent proteins. Preferably, one fluorescent moiety is capable of emitting light of a wavelength capable of exciting the other fluorescent moeity. FRET reporter systems preferably comprise a first chimeric protein comprising either Smac or XIAP, ML-IAP or a Smac binding fragment thereof and a fluorescent protein and a second chimeric protein comprising the other binding partner and another fluorescent protein. It is then possible to detect the complex formation through the occurrence of FRET (Fluorescence Resonance Energy Transfer). BRET or FRET according to the present invention may for example be performed essentially as described in (Nicolas B, R Jockers, and T Issad *Trends in Pharmacological Sciences* 23 (8):351-354, 2002; and/or A. Roda, M. Guardigli, P. Pasini, and M. Mirasoli. *Anal. Bioanal. Chem.* 377 (5):826-833, 2003)

The detectable output of BRET or FRET is luminescence, such as fluorescence or bioluminescence. Bioluminescence may be detected by any conventional methods, for example with the aid of a Plate reader or a fluorometer. Fluorescence may for example be detected using FABS (fluorescence activated bead sorter), a plate reader, a fluorescence microscope or the like.

Thus in one embodiment Smac may be linked to a bioluminescent or fluorescent moiety, whereas XIAP or ML-IAP or a Smac binding fragment thereof may be linked to a different bioluminescent or fluorescent moiety. One useful assay is described in example 4 herein below. Preferred compounds according to the present invention are compounds giving rise to a BRET signal which is equal to or lower than the BRET signal of the positive control in an assay performed as described in example 4. Thus preferred compounds may give rise to a BRET signal which is equal to or lower than the BRET signal of the positive control in an assay performed as described in example 4 even when said compound is added at a lower concentration, such as at a concentration which is less than 80%, such as less than 70%, for example less than 60%, such as less than 50% of the positive control.

Another useful assay for determining binding between Smac and XIAP or ML-IAP or a Smac binding fragment thereof is proximity ligation. Proximity ligation may for example be carried out as described in Frederiksson et al. Nature Biotechnology 2002, 20: 473; Gullberg et al. Curr Opinion Biotechnology 2003, 14: 82. yet another useful assay is a "two-hybrid system". Suitable two-hybrid systems are well described in the art, see for example U.S. Pat. No. 5,283, 173.

Enzyme complementation assays are also useful for detecting binding be between Smac and XIAP or ML-IAP or a Smac binding fragment thereof. Enzyme complementation assays may for example be performed as described by Remy I, Michnick S W Proc Natl Acad Sci USA 1999 May 96:5394-9.

The cells to be used with the present invention may be any useful cells available or prepared for the purpose. Preferably, the cells are selected from the group consisting of mammalian cells. For example the cells may be human cells. Adherent cells may preferably be cultivated directly on resin beads optionally comprising an adhesion compound.

In one embodiment of the invention the cells have been genetically or otherwise modified in order to enhance their usability with the present invention. For example nucleic acids encoding chimeric proteins as used in the assays described above may be introduced into the cells. The modification may be stable or only transient or a mixture of both. Methods of modifying cells are well known to the skilled person.

In one embodiment the invention relates to methods of identifying a compound capable of inducing or facilitating apoptosis in living cells, such as capable of inducing or facilitating apoptosis in tumour cells, preferably capable of inducing apoptosis.

Induction/facilitation of apoptosis may be determined by a number of methods well known to the skilled person.

Preferably, the compounds of the invention are capable of altering the activity of one or more caspases, preferably the compounds are capable of altering the activity of one or more caspases within a living cell in vivo or ex vivo. It is preferred that the compound is capable of inducing the activity of said caspase. Preferred caspases are Caspase 3 or 7. The Caspase activity may be determined by any conventional assay available to the skilled person. In one embodiment the assay will involve the steps of a. Providing a compound according to the invention
b. Providing a composition or a cell comprising caspase
c. Incubating said composition or said cell with the compound, wherein said composition or said cell optionally is subjected to an apoptosis promoting treatment
d. Determining activity of said caspase Preferably, the assay is performed using a cell comprising caspase, such as a mammalian cell, for example a mammalian tumour cell. Preferably, said cell comprises Caspase 3 and/or 7.

The apoptosis promoting treatment may be contacting the composition with an inducer of apoptosis. The inducer of apoptosis may be any compound known to be capable of inducing apoptosis, for example the compound may be staurosporine (STS). Alternatively, the apoptosis promoting treatment may be illumination with radiation, such as with UV-light with a predetermined wavelength and intensity.

Caspase activity may in one embodiment be determined by providing a substrate for said caspase and determining whether said substrate is cleaved. Useful caspase substrates are known to the skilled person and several caspase substrates are commercially available, for example from Beckman Coulter Inc. Preferred Caspase substrates are Caspase 3 and/or 7 substrates. It is also preferred that cleavage of the substrates is readily detectable. Thus fluorogenic substrates comprising a quenching group which may be cleaved of by caspases may be useful. Cleavage of such substrate can simply be detected by determining fluorescence. Non-limiting examples of fluorogenic caspase substrates are the CellProbe HT Caspase 3/7 Whole Cell Assay, Beckman Coulter, Inc, or any of the substrates described in U.S. Pat. No. 6,342,611.

A non-limiting example of a useful Caspase assay is given in example 5 herein below.

Induction/facilitation of apoptosis may also be determined by determining cell growth, for example cell growth in tumour cells, such as cells expressing high levels of XIAP or ML-IAP. In one example cells expressing high levels of XIAP or ML-IAP may be contacted with TRAIL. Preferably, said cell will grow in the absence of compound. In one embodiment preferred compounds according to the invention are compounds, which are capable of inhibiting growth of such cells, wherein growth is determined by counting the number of cells. More preferably, the compound is capable of reducing the number of cells. Even more preferable the compound is capable at inhibiting growth or reducing the number of cells when added to cells at a concentration of less than 0.9 µM, preferably less than 0.4 µM, such as less than 0.3 µM, for example less than 0.2 µM, such as less than 0.1 µM, such as in the range of 0.01 to 0.3 µM, for example in the range of 0.05 to 0.2 µM.

Induction/facilitation of apoptosis may also be determined by determining membrane permeability. Membranes of apoptotic cells become permeable over time and preferred compounds according to the present invention are compounds capable of inducing apoptosis as determined by induction of membrane permeability in cells.

Numerous useful assays for determining membrane stability are known to the skilled person. In general the assays will involve contacting living cells with a test compound and determining membrane permeability of said cells. The membrane permeability may for example be determined by determining diffusion of a compound into or out of cells. For example cells expressing a detectable compound, such as GFP, may be used and diffusion of GFP out of the cells may be used as a measure for membrane permeability. In another example a detectable compound, such as a fluorescent compound or a dye may be added to the growth medium of cells and influx of uptake of said compound to cells may be used as a measure for membrane permeability. A combination of several compounds can also be envisaged. In one embodiment of the invention cells may be cultivated directly on resin beads linked to test compounds. Methods for cultivating cells on resin beads are for example described in PCT application PCT/DK2005/00347 for example in the section "Cell attachment to resin beads and cell cultivation" starting on p. 28. Methods for preparing resin beads linked to test compounds are for example described in PCT application PCT/DK2005/00347 for example in the section "Library of test compounds". Resin beads comprising cells with increased membrane permeability may be selected, for example resin comprising cells with similar or increased membrane permeability as compared to a reference compound may be selected. Compounds linked to selected resin beads will be preferred according to the present invention. A non-limiting example of a method for selecting resin beads linked to preferred compounds according to the invention is described in Example 7 herein below.

In addition preferred compounds according to the invention are capable of inhibiting the growth of cancer cells. In particular, it is preferred that the compounds are capable of inhibiting the growth of cancer cells in vivo.

Several assays for assessing inhibition of growth of cancer cells in vivo are known to the skilled person and may be employed for evaluating the compounds of the invention.

Frequently, the assays will involve determining the size (such as the weight) of a solid tumour in a test animal, such as a mouse, before and after administration of the compound. The tumour may be spontaneous. It may also be established may injection of tumour cells into test animals, such as nude mice.

The compound may be administered to the test animal alone or in combination with another compound. For example the compound may be administered in combination with an anticancer agent, such as any of anticancer agents mentioned herein below, for example taxol.

In one embodiment the preferred compounds give rise to a reduction in tumour weight of at least 50%, preferably at least 60%, more preferably at least 70%, even more preferably at least 80%, such as at least 85% in mice after 29 days compared to control mice. If more the compounds are administered together with a chemotherapeutic compound, it is preferred that the control mice receive said chemotherapeutic compound. More preferably, the method of determining reduction in tumour weight is performed essentially as described in Example 8.

It is furthermore preferred that the compounds are not toxic in the sense that it is preferred that the compounds are not lethal in therapeutic effective doses and that the compounds do not cause severe side effects in therapeutic effective doses. It is thus preferred that the compounds do not cause immediate death at a dose of at least 10 mg/kg, such as in the range of 10 to 500 mg/kg, preferably the compounds do not cause immediate death at a dose of at least 20 mg/kg, such as in the range of 20 to 500 mg/kg, even more preferably the compounds do not cause immediate death at a dose of at least 30 mg/kg, for example in the range of 30 to 500 mg/kg when injected i.v. It is also preferred that the compounds do not cause immediate death at a dose of at least 30 mg/kg for example in the range of 30 to 500 mg/kg, preferably the compounds do not cause immediate death at a dose of at least 50 mg/kg for example in the range of 50 to 500 mg/kg, more preferably the compounds do not cause immediate death at a dose of at least 100 mg/kg for example in the range of 100 to 500 mg/kg, when injected i.p, In addition it is preferred that the compounds do not cause significant weight loss and/or deposit of fibrous material around dosing area when administered at a dose of at least 100 mg/kg/hour, for example in the range of 100 to 500000 μg/kg/hour, more preferably when administered at a dose of at least 500 μg/kg/hour, for example in the range of 0.5 to 500 mg/kg/hour, even more preferably when administered at a dose of at least 1 mg/kg/hour, for example in the range of 1 to 500 mg/kg/hour, yet more preferably when administered at a dose of at least 3 mg/kg/hour, for example in the range of 3 to 500 mg/kg/hour for example 24 hours.

Identification of Compound

In embodiments of the invention, wherein a resin bead comprising a compound is selected by screening as described above, the compound, which preferably is remaining after partial release on said bead may be identified. Preferably, only one resin bead is used at a time. Thus if said resin bead only comprises one library member in one or more copies, then only one compound is identified at a time.

The compound can be identified using a variety of methods. The compound may be cleaved off the resin bead, and then analyzed using IR, MS, or NMR. For NMR analysis, larger beads containing approximately 5 nmoles of material are preferably used for the acquisition of 1-dimensional (1-D) and 2-dimensional (2-D) NMR spectra. Furthermore, these spectra can be attained using high-resolution MAS NMR (magic angle spinning nuclear magnetic resonance) techniques. Alternatively, high resolution-MAS NMR spectra can be acquired while the ligand is still bound to the solid support, as described for example, in Goffredsen et al., 2000, J. Chem. Soc., Perkin Trans., 1: 1167-71. The compound may also be identified by release of the compound and fragmentation by MS-MS in MALDI or electrospray mode.

In a preferred embodiment of the invention the compound(s) comprised within selected resin beads are identified using mass spectrometry (MS). MS can be used alone to identify the compounds. The compounds can be cleaved from the resin bead, optionally by cleaving the cleavable linker, the molecular mass determined, and subsequently fragmented into sub-species to conclusively determine the structure by combination with knowledge of contained structures in the library. MS-based methods of compound identification are useful in this invention, as they require very little material, and can utilise pico- to femtomole amounts of compound.

Pharmaceutical Compositions and Clinical Conditions

The present invention also relates to above-mentioned compounds as well as pharmaceutically acceptable salts thereof for use as medicaments. It will be apparent to one of skill in the art when a compound of the invention can exist as a salt form, especially as an acid addition salt or a base addition salt. When a compound can exist in a salt form, such salt forms are included within the scope of the invention. Although any salt form may be useful in chemical manipulations, such as purification procedures, only pharmaceutically acceptable salts are useful for pharmaceutical products.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleat, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

The present invention further includes pharmaceutical compositions comprising a pharmaceutically effective amount of one or more of the above-described compounds as active ingredient. Pharmaceutical compositions according to the invention are suitable for enteral, such as oral or rectal, and parenteral administration to mammals, preferably human being, for the treatment of proliferative diseases, including tumors, especially cancerous tumors, and other cancers alone or in combination with one or more pharmaceutically acceptable carriers.

The inventive compounds are useful for the manufacture of pharmaceutical compositions having an effective amount the compound in conjunction or admixture with excipients or carriers suitable for either enteral or parenteral application. Examples include tablets and gelatin capsules comprising the active ingredient together with (a) diluents; (b) lubricants, (c) binders (tablets); if desired, (d) disintegrants; and/or (e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. The compositions are prepared according to conventional mixing, granulating or coating methods, respectively, and contain preferably about 1 to 50% of the active ingredient.

More generally, the present invention also relates to the use of the compounds of the invention for the manufacture of a medicament, in particular for the manufacture of a medicament for the treatment of proliferative diseases.

Also contemplated are methods for treatment of a proliferative disease comprising administering the compound(s) according to invention to an individual in need thereof.

Suitable formulations also include formulations for parenteral administration such as aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried(lyophilized) condition requiring only the addition of the sterile liquid carrier, for example, water for injections, immediately prior to use.

Extemporaneous injection solutions and suspensions may be prepared from sterile powders, granules and tablets of the kind previously described.

The pharmaceutical composition contains a pharmaceutically effective amount of the present active agent along with other pharmaceutical acceptable excipients, carriers, fillers, diluents and the like. The term therapeutically effective amount as used herein indicates an amount necessary to administer to a host to achieve a therapeutic result, especially an anti-tumor effect, e.g., inhibition of proliferation of malignant cancer cells, benign tumor cells or other proliferative cells.

As discussed above, the compounds of the present invention are useful for treating proliferative diseases. Thus, the present invention further relates to a method of treating a proliferative disease which comprises administering a therapeutically effective amount of a compound of the invention to a mammal, preferably a human, in need of such treatment.

A proliferative disease is mainly a tumor disease (or cancer) (and/or any metastases).

The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is when administered alone or in combination with other anticancer agents preferably selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

The compounds of the present invention may be administered alone or in combination with other anticancer agents, such as compounds that inhibit tumor angiogenesis, for example, the protease inhibitors, epidermal growth factor receptor kinase inhibitors, vascular endothelial growth factor receptor kinase inhibitors and the like; cytotoxic drugs, such as antimetabolites, like purine and pyrimidine analog antimetabolites, carboplatin, cisplatin, cyclophosphamide, iphosphamide, hexamethylmelamine, doxorubicin, epirubicin, etopiside (VP-16), teniposide (VM-26), vincristine, vindecine, taxans, paclitaxel, irinotecan, nimustine, lomustine, BCNU, farnesyl transferase inhibitors, 5-fluoruracil±leucovorin, topoisomerase inhibitor I and II and Temozolamide; antimitotic agents like microtubule stabilizing drugs and antimitotic alkaloid; platinum coordination complexes; anti-tumor antibiotics; alkylating agents, such as nitrogen mustards and nitrosoureas; endocrine agents, such as adrenocorticosteroids, androgens, anti-androgens, estrogens, anti-estrogens, aromatase inhibitors, gonadotropin-releasing hormone agonists and somatostatin analogues and compounds that target an enzyme or receptor that is overexpressed and/or otherwise involved a specific metabolic pathway that is upregulated in the tumor cell, for example ATP and GTP phosphodiesterase inhibitors, histonedeacetylase inhibitors, protein kinase inhibitors, such as serine, threonine and tyrosine kinase inhibitors, for example, Abelson protein tryosine kinase and the various growth factors, their receptors and kinase inhibitors therefore, such as, epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors and the like; methionine aminopeptidase inhibitors, proteasome inhibitors, andcyclooxygenase inhibitors, for example, cyclooxygenase-1 or -2 inhibitors.

EXAMPLES

Example 1

General Methods for Solid Phase Peptide Synthesis (SPPS)

General for Chemical Synthesis:
All chemicals described are commercially available and used without further purification. All solvents were HPLC-grade. PEGA—resins were purchased from VersaMatrix A/S, Copenhagen. Each washing step lasted 2 min unless otherwise stated. Purifications were performed on a standard reverse phase HPLC using gradients of acetonitrile-water with various amounts of TFA.
Coupling of HMBA Linker to PEGA—Resin:
Dry PEGA—resin was swelled in DCM and washed with DMF (3×). 3.0 eq. HMBA, 2.9 eq. TBTU and 6 eq. NEM were mixed in appropriate DMF and allowed to react for 10 min. The mixture was added to resin and after 2 h the resin was washed with DMF (6×), DCM (6×) and lyophilised.
General Procedure for Coupling of Amino Acid to HMBA-linker:
Dry PEGA—resin with HMBA-linker was swelled in dry DCM. 3.0 eq. Fmoc-protected amino acid, 2.25 eq. MeIm and 3.0 eq. MSNT were mixed in appropriate amount of dry DCM and added to resin. After 1 h the resin was washed with DCM (3×) and the coupling was repeated as above once. After coupling for 1 h the resin was washed with DCM (6×), DMF (6×), DCM (6×) and lyophilised.
General SPPS Coupling Procedure:
The terminal amino acid on the resin was Fmoc-deprotected by treatment with 20% piperidine in DMF (1×2 min+ 1×18 min) followed by washing with DMF (6×). 3.0 eq. Fmoc-protected amino acid, 2.9 eq. TBTU and 6.0 eq. NEM were mixed in appropriate amount of DMF and allowed to react for 10 min. The mixture was added to the resin and after 2 h the resin was washed with DMF (6×).
General Side Chain Deprotection Procedure:
Dry PEGA—resin with acid stable linker and compound and/or peptide was swelled in $H_2O$ and the side chains was deprotected with 95% TFA (aq) (2×15 min). If Pmc groups were present cleavage time was 6 h. The resin was washed with $H_2O$ until washing water had pH=5-7. The resin was then washed with DMF (10×), DCM (10×) and lyophilised.
General HMBA Cleavage Procedure:
Dry PEGA—resin with HMBA linker and attached compound was swelled in water and NaOH (aq.) 0.1 M was added. After 2 h HCl (aq.) 0.1 M was used for neutralisation and then AcN was added until the $H_2O$/AcN ratio was 1:1 by volume. The resin was filtered off and the liquid was used direct for RP-HPLC or/and Q-TOF MS analysis if needed.

The above general procedures are used for solid phase peptide synthesis in the following examples unless otherwise specified.

Example 2

Formation of a "Tetrapeptide" Library Linked Via an Internal Amide Nitrogen

Synthesis of FmocGly/AllocGly (ratio ~1:1) Modified PEGA 1900 Beads
PEGA 1900 beads (300-500 µm, 0.24 mmol $NH_2$/g) (4 g, 0.96 mmol ~1 eq)) were treated with a 1:1 TBTU coupling mixture of FmocGlyOH (2 eq) and AllocGlyOH (2 eq), NEM (17 eq) and TBTU (3.8 eq). Coupling time was 3.5 h. Beads were washed 10× with DMF.
Coupling of Aldehyde Photolinker to the "Core" Fmoc-Glycine.
FmocGly/AllocGly beads were standard Fmoc deprotected with 20% piperidine in DMF leaving the Alloc glycine untouched. Then standard TBTU coupling of the aldehyde photolinker (4-(4-formyl-2-methoxy-5-nitrophenoxy)butanoic acid) to the deprotected glycine (1 eq=0.48 mmol). After coupling, the beads were washed with DMF and DCM and lyophilized.

TABLE 1

Phenylethylamines used for reductive amination of aldehyde linker

| 1 | 2 | 3 | 4 | 5 |
|---|---|---|---|---|
| (phenyl)-$NH_2$ | F-(phenyl)-$NH_2$ | F-(phenyl)-$NH_2$ | Cl-(phenyl)-$NH_2$ | MeO-(phenyl)-$NH_2$ |
| 121.18 g/mol | 139.17 g/mol | 139.17 g/mol | 155.63 g/mol | 151.21 g/mol |
| d: 0.965 | d: 1.061 | d: 1.066 | d: 1.119 | d: 1.033 |

TABLE 2

| | Compounds used for BTC coupling | | | |
|---|---|---|---|---|
| Well number | 1 | 2 | 3 | 4 |
| Structure | BocHN, FmocN, pyrrolidine-COOH | BocHN, FmocN, pyrrolidine-COOH | BocHN, FmocN, pyrrolidine-COOH | BocHN, FmocN, pyrrolidine-COOH |
| Mw (g/mol) | 452.50 | 452.50 | 452.50 | 452.50 |
| Mol × 10$^6$ | 36 | 36 | 36 | 36 |
| Weight (mg) | 16.3 | 16.3 | 16.3 | 16.3 |
| Well number | 5 | 6 | 7 | 8 |
| Structure | BocHN, FmocN, pyrrolidine-COOH | BocHN, FmocN, pyrrolidine-COOH | BocHN, FmocN, pyrrolidine-COOH | BocHN, FmocN, pyrrolidine-COOH |
| Mw (g/mol) | 452.50 | 452.50 | 452.50 | 452.50 |
| Mol × 10$^6$ | 36 | 36 | 36 | 36 |
| Weight (mg) | 16.3 | 16.3 | 16.3 | 16.3 |
| Well number | 9 | 10 | 11 | 12 |
| Structure | BocHN, FmocN, pyrrolidine-COOH | BocHN, FmocN, pyrrolidine-COOH | FmocN, pyrrolidine-COOH | FmocN, pyrrolidine-COOH |
| Mw (g/mol) | 452.50 | 452.50 | 337.67 | 337.67 |
| Mol × 10$^6$ | 36 | 36 | 36 | 36 |
| Weight (mg) | 16.3 | 16.3 | 12.1 | 12.1 |
| Well number | 13 | 14 | 15 | 16 |
| Structure | Fmoc-cyclobutane-COOH | N-Fmoc-piperidine-3-COOH (R/S) | tetrahydroisoquinoline-3-COOH NFmoc | FmocHN-cyclopentane-COOH |
| Mw (g/mol) | 323.34 | 351.40 | 399.44 | 351.40 |
| Mol × 10$^6$ | 36 | 36 | 36 | 36 |
| Weight (mg) | 11.6 | 12.7 | 14.4 | 12.7 |

TABLE 2-continued
| | Compounds used for BTC coupling | | | |
|---|---|---|---|---|
| Well number | 17 | 18 | 19 | 20 |
| Structure | 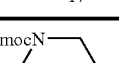 | 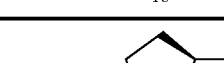 | 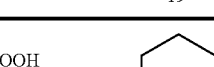 | 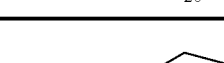 |
| Mw (g/mol) | 427.49 | 413.47 | 379.46 | 565.72 |
| Mol × $10^6$ | 36 | 36 | 36 | 36 |
| Weight (mg) | 15.4 | 14.9 | 13.7 | 20.4 |
TABLE 3
| Compounds used for acylation in wells 1-10. | | | | |
|---|---|---|---|---|
| 1 | 2 | 3 | 4 | 5 |
|  |  |  |  |  |
| Mw: 132.59 d: 1.091 | Mw: 130.53 d: 1.324 | Mw: 154.60 d: 1.167 | Mw: 158.56 d: 1.342 | Mw: 146.96 d: 1.096 |
TABLE 3-continued
| Compounds used for acylation in wells 1-10. | | | | |
|---|---|---|---|---|
| 6 | 7 | 8 | 9 | 10 |
|  |  |  |  |  |
| Mw: 120.58 d: 0.989 | Mw: 134.61 d: 0.969 | Mw: 106.55 d: 1.107 | Mw: 104.54 d: 1.152 | Mw: 78.50 d: 1.104 |
TABLE 4
| | Compounds used for TBTU coupling | | | |
|---|---|---|---|---|
| Member number | 1 | 2 | 3 | 4 |
| Structure | 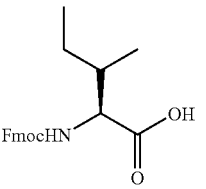 | 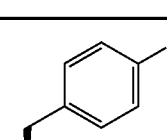 | 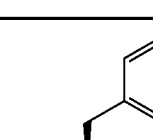 | 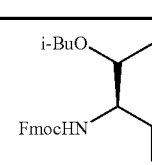 |
| Mw (g/mol) | 353.41 | 379.46 | 393.48 | 411.45 |
| Mol × $10^6$ | 36 | 36 | 36 | 36 |
| Weight (mg) | 12.7 | 13.7 | 14.1 | 14.8 |
| Member number | 5 | 6 | 7 | 8 |
| Structure | 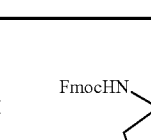 | | | |

TABLE 4-continued

Compounds used for TBTU coupling

| | | | | |
|---|---|---|---|---|
| Mw (g/mol) | 405.42 | 387.43 | 397.46 | 351.40 |
| Mol × 10$^6$ | 36 | 36 | 36 | 36 |
| Weight (mg) | 14.6 | 13.9 | 14.3 | 12.6 |

| Member number | 9 | 10 | 11 | 12 |
|---|---|---|---|---|
| Structure | (Fmoc-Leu-OH) | (Fmoc-His(Boc)-OH) | (Fmoc-Glu(OtBu)-OH) | (Fmoc-Asn(Trt)-OH) |
| Mw (g/mol) | 353.41 | 477.51 | 425.47 | 596.67 |
| Mol × 10$^6$ | 36 | 36 | 36 | 36 |
| Weight (mg) | 12.7 | 17.2 | 15.3 | 21.5 |

| Member number | 13 | 14 | 15 | 16 |
|---|---|---|---|---|
| Structure | (Fmoc-1-aminocyclohexane carboxylic acid) | (Fmoc-azetidine-2-carboxylic acid) | (Fmoc-Gln(Trt)-OH) | (Fmoc-3,4-dimethoxy-Phe-OH) |
| Mw (g/mol) | 565.42 | 323.34 | 610.70 | 447.49 |
| Mol × 10$^6$ | 36 | 36 | 36 | 36 |
| Weight (mg) | 20.4 | 11.6 | 22.0 | 16.1 |

| Member number | 17 | 18 | 19 | 20 |
|---|---|---|---|---|
| Structure | (Fmoc-Aib-OH) | (Fmoc-Ser(tBu)-OH) | (Fmoc-β-(2-thienyl)-Ala-OH) | (Fmoc-Ala-OH) |
| Mw (g/mol) | 325.36 | 383.44 | 393.46 | 311.33 |
| Mol × 10$^6$ | 36 | 36 | 36 | 36 |
| Weight (mg) | 11.7 | 13.8 | 14.2 | 11.2 |

TABLE 5

Compounds used for TBTU coupling of amino acids and acylation with acyl chlorides

| Member number | 1 | 2 | 3 | 4 |
|---|---|---|---|---|
| Structure | (Boc-amino acid) | (Boc-azetidine-2-carboxylic acid) | (Boc-amino acid) | (Boc-Ala-OH) |
| Mw | 203.24 | 201.22 | 189.21 | 189.21 |
| Mol × 10$^6$ | 36 | 36 | 36 | 36 |
| Weight (mg) | 7.3 | 7.2 | 6.8 | 6.8 |

TABLE 5-continued

Compounds used for TBTU coupling of amino acids and acylation with acyl chlorides

| Member number | 5 | 6 | 7 | 8 |
|---|---|---|---|---|
| Structure | BocHN-CH(Et)-COOH | BocHN-C(Me)₂-COOH | BocHN-CH(CH₂-O-t-Bu)-COO⁻·DCHA⁺ | BocHN-CH(CH₂-O-t-Bu)-COO⁻·DCHA⁺ |
| Mw (g/mol) | 203.24 | 203.24 | 442.63 | 442.63 |
| Mol × 10⁶ | 36 | 36 | 36 | 36 |
| Weight (mg) | 7.3 | 7.3 | 15.9 | 15.9 |

| Member number | 9 | 10 | 11 | 12 |
|---|---|---|---|---|
| Structure | BocHN-CH₂-COOH | BocHN-CH(CH₂-NHBoc)-COO⁻·DCHA⁺ | BocHN-CH(sec-Bu)-COOH | BocHN-CH(iBu)-COOH |
| Mw (g/mol) | 175.18 | 485.66 | 231.29 | 231.29 |
| Mol × 10⁶ | 36 | 36 | 36 | 36 |
| Weight (mg) | 6.3 | 17.5 | 8.3 | 8.3 |

| Member number | 13 | 14 | 15 | 16 |
|---|---|---|---|---|
| Structure | BocHN-CH(iPr)-COOH | Boc-Pro-OH | BocHN-CH(CH(CH₃)-O-t-Bu)-COOH | t-Bu-CH₂-C(O)Cl |
| Mw (g/mol) | 217.26 | 215.25 | 275.34 | 134.60 |
| Mol × 10⁶ | 36 | 36 | 36 | 36 |
| Weight (mg) | 7.8 | 7.7 | 9.9 | 16.2 (0.017 mL) |

| Member number | 17 | 18 | 19 | 20 |
|---|---|---|---|---|
| Structure | iBu-C(O)Cl | cyclopropyl-C(O)Cl | iPr-C(O)Cl | CH₃-C(O)Cl |
| Mw (g/mol) | 120.58 | 104.53 | 106.55 | 78.50 |
| Mol × 10⁶ | 120 | 120 | 120 | 120 |
| Weight (mg) | 14.4 (0.015 mL) | 12.6 (0.011 mL) | 12.8 (0.013 mL) | 9.4 (0.009 mL) |

Library Synthesis:

Step 1, Reductive Amination of Photo Linker Aldehyde:

5 portions of the above beads (0.8 g dry beads) were placed in 5 syringes of 5 mL. The beads were swollen in DMF and phenylethylamines (see Table 1) were coupled to the free aldehyde on the photolinker by reductive amination as follows: 0.8 g dry beads is 96 μmols ~1 eq were pre-treated with the reaction solvent (DMF/HOAc/TEOF/EtOH, 1:1:1:1). Then to each syringe was added one of the five phenylethylamines (20 eq) dissolved in the reaction solvent (400 μL), and the same solvent was added so the beads were covered. After 0.5 h NaBH₃CN (20 eq) was added and the beads stirred cautiously until all dissolved. After 1 h another portion of NaBH₃CN (20 eq) was added and the mixture left for additional 2 h. The beads were washed with DMF (10×), DCM (10×), MeOH (10% HOAc) (2×), MeOH (10×), DMF (20% pip) (2×), and DMF (10×), DCM (10×). The 5 samples were lyophilized over night.

Step 2, Mix and Split of Phenylethyl Amines:

0.4 g of each of the 5 bead samples from above were swelled in DMF, mixed and transferred to a custom made 20-well library synthesizer such that each well contained approximate equal amounts of beads.

Step 3, BTC Coupling of First Amino Acid:

Total amount of beads=2.0 g ~0.24 mmol gives 12 μmol NH/well ~1 eq.

BTC-couplings from 11 different amino acids as shown in Table 2 was made as follows: Beads were pre-treated with a 1:1 vol % THF/DIPEA solution for 5 minutes and drained. Of each amino acid in Table 2, 3 eq (36 μmol) was dissolved in dry THF (200 µL) and BTC (1.67 eq) added as 200 µL of a freshly made stock solution in dry THF. Then 2,4,6-collidine (14 eq), as 200 µL of a freshly made stock solution in dry THF, was added and the resulting 20 suspensions left for 5 minutes. Each suspension was added to the respective well and after short mixing the synthesizer was sealed and left over night with gentle shaking. Next morning the beads were washed with THF (10×) and DMF (10×) without mixing the wells.

Step 4, Acylation of Well 1-10:

Beads in well 1-10 were washed with DCM (10×) and Boc deprotected with 30% TFA in DCM followed by wash with DCM (10×), DCM (5% DIPEA), DMF, and DCM (10×). From each of the 10 acyl chlorides in Table 3 was made a solution of 10 eq acyl chloride (120 µmol) and DIPEA (20 eq) in dry DCM (400 µL) containing catalytic amounts of DMAP. The resulting solutions were added to well 1-10 and left with gentle shaking for 1 h. The reaction was repeated. After end reactions the beads were washed with DCM (10×), and DMF (10×).

Step 5, Removal of Fmoc Protection Groups:

Well 1-20 were standard Fmoc deprotected, followed by wash with DMF (10×).

Step 6, Mix and Split of the 20 Wells

The content of the 20 wells was thoroughly mixed and re-distributed equally into the wells.

Step 7, Coupling of Second Amino Acid (20 Amino Acids):

To each well was coupled an amino acid according to Table 4 by a standard TBTU coupling. Coupling time 5 h. After end reaction the beads were washed with DMF (10×).

Step 8, Coupling of Third Amino Acid/Acyl Chloride (15 Amino Acids-5 Acyl Chlorides):

The beads in all wells were standard Fmoc deprotected and for well 1-15 standard TBTU coupled with the Boc-protected amino acids in Table 5. For wells 16-20 the beads were first washed with DCM (10×) and the N-terminal amines acylated with the five acyl chlorides listed in Table 5 (entry 16-20) analogous to step 4. After couplings all wells were washed with DMF (10×).

Step 9, Alloc Deprotection of Second "Core" Glycine:

The beads from the 20 wells were all combined in a 50 mL syringe and washed with $CHCl_3$ (5×) and with Ar-degassed $CHCl_3$ containing 5% HOAc and 2.5% NEM (5×). A solution of $Pd(PPh_3)_4$ (3 eq, 0.72 mmol) in Ar-degassed $CHCl_3$ containing 5% HOAc and 2.5% NEM (10 mL) was added to the beads and after bobling a few minutes with Ar the syringe was sealed with parafilm and left for 2 h. The beads were washed with $CHCl_3$ (10×), DMF (10×), DMF (5% DIPEA, 5% sodium diethyldithiocarbamate)(5×), MeOH (10×), DMF DMF (20×). Kaiser test was positive.

Step 10, Attachment of HMBA Linker:

According to the standard procedure above.

Step 11, MSNT Coupling of FmocGlyOH:

According to the standard procedure above.

Step 12, TBTU Coupling of FmocLys(Fmoc)OH

According to the standard procedure above.

Step 13, Attachment of Adhesion Peptides

Adhesion peptides were synthesized on the Fmoc-protected lysine such that the final beads had two adhesion peptides pr. library molecule. One batch of the library was attached adhesion peptide A, and a second batch with adhesion peptide B.

Adhesion peptide A: (Boc-D-Ala-D-Arg(Pmc)-D-Lys(Boc)-D-Arg(Pmc)-D-Ile-D-Arg(Pmc)-D-Gln(Trt)-Gly-:

Fmoc deprotection of lysine residues: According to the standard procedure.

Coupling: The adhesive peptide was synthesized directly (stepwise) on the library beads using the general SPPS coupling procedure.

Alternative method: The purified peptide (Boc-D-Ala-D-Arg(Pmc)-D-Lys(Boc)-D-Arg(Pmc)-D-Ile-D-Arg(Pmc)-D-Gln(Trt)-L-Gly-OH) (3 eq) was coupled to the lysine $NH_2$ groups using the general SPPS coupling procedure.

Adhesion peptide B: (Fmoc-D-Arg(Pmc)-D-Gln(Trt)-D-Arg(Pmc)-D-Ile-D-Arg(Pmc)-: Analogous to synthesis of adhesion peptide A.

Deprotection of Adhesion and Library Peptides

Final deprotection of protecting groups was performed according to the general procedure described above yielding the TCOB libraries ready for testing.

Example 3

Synthesis of a 42.000 Member Tetrapeptide Library on Beads with Fixed Adhesion Peptide This example describes the preparation of a photo cleavable library of tetrapeptides (~42.000 members) on resin beads containing a base cleavable "cell adhesive peptide". This "two compound one bead" (TCOB) library may be used for in vivo screening of the tetrapeptides for e.g. antagonists action on the X-IAP or ML-IAP receptor.

Formation of a "Tetrapeptide" Library Linked Via a Terminal Amide Nitrogen

Synthesis of FmocGly/AllocGly (ratio ~1:1) modified PEGA 1900 beads PEGA 1900 beads (300-500 µm, 0.24 mmol $NH_2$/g) (4 g, 0.96 mmol 1 eq)) were treated with a 1:1 TBTU coupling mixture of FmocGlyOH (2 eq) and AllocGlyOH (2 eq), NEM (17 eq) and TBTU (3.8 eq). Coupling time was 3.5 h. Beads were washed 10× with DMF.

Coupling of "Holmes" Photolinker to the "Core" Fmoc-Glycine.

FmocGly/AllocGly beads were standard Fmoc deprotected with 20% piperidine in DMF leaving the Alloc glycine untouched. Then standard TBTU coupling of the photolinker (4-[(1-Fmoc-aminoethyl)-2-methoxy-5-nitrophenoxy]butanoic acid) (3 eq) to the deprotected glycine (1 eq=0.48 mmol). After coupling, the beads were washed with DMF and DCM and lyophilized.

Preparation of Tetrapeptide Library with 44.000 Members

The beads containing the Fmoc protected photo linker (2.00 g) were placed in a custom made 20 well synthesizer with approximately equal amounts in each well. After general Fmoc deprotection four couplings using the general SPPS TBTU coupling procedure were performed using a split and mix protocol. Amino acids (20×20×10×10) used for couplings are given in Tables 6 to 9. For the $3^{rd}$ and $4^{th}$ coupling each amino acid is added to 2 wells. Protection groups are left on the peptides after end couplings.

TABLE 6
Amino acids used for the 1st coupling.
| Member number | 1 | 2 | 3 | 4 |
|---|---|---|---|---|
| Structure | 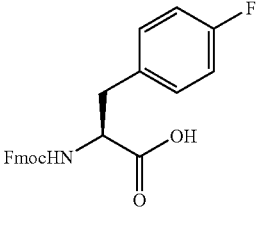 | 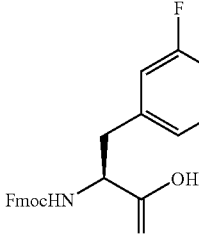 | 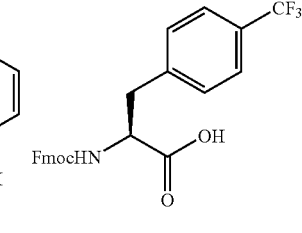 | 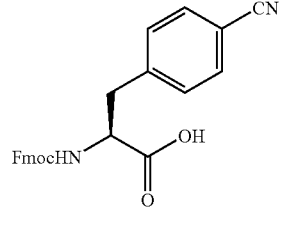 |
| Mw (g/mol) | 405.42 | 405.42 | 455.43 | 412.44 |
| micromol | 36 | 36 | 36 | 36 |
| Weight (mg) | 14.6 | 14.6 | 16.9 | 14.8 |
| Member number | 5 | 6 | 7 | 8 |
|---|---|---|---|---|
| Structure | 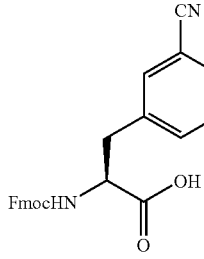 | 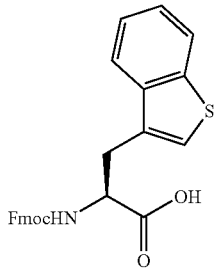 | 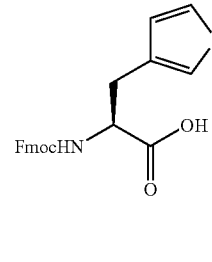 | 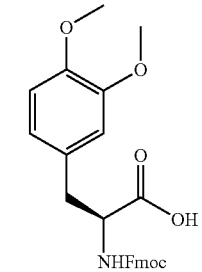 |
| Mw (g/mol) | 412.44 | 443.51 | 393.46 | 447.48 |
| micromol | 36 | 36 | 36 | 36 |
| Weight (mg) | 14.8 | 15.9 | 14.1 | 16.1 |
| Member number | 9 | 10 | 11 | 12 |
|---|---|---|---|---|
| Structure | 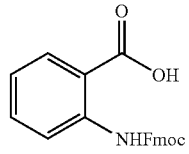 | 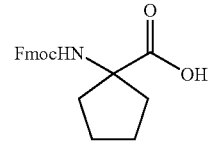 | 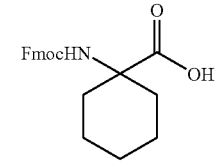 | 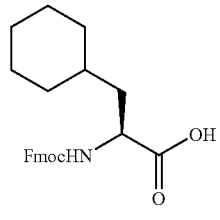 |
| Mw (g/mol) | 359.37 | 351.40 | 365.42 | 393.48 |
| micromol | 36 | 36 | 36 | 36 |
| Weight (mg) | 12.9 | 12.7 | 13.1 | 14.1 |
| Member number | 13 | 14 | 15 | 16 |
|---|---|---|---|---|
| Structure | 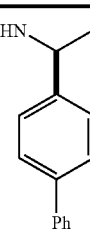 | 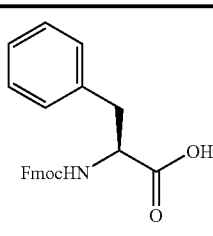 | 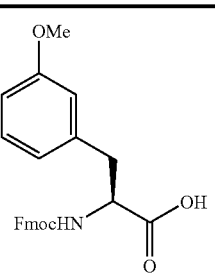 | 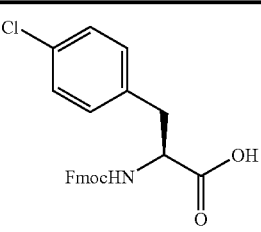 |

TABLE 6-continued
| Amino acids used for the 1st coupling. | | | | |
|---|---|---|---|---|
| Mw (g/mol) | 463.52 | 387.43 | 417.45 | 421.87 |
| micromol | 36 | 36 | 36 | 36 |
| Weight (mg) | 16.7 | 13.9 | 15.0 | 15.2 |
| Member number | 17 | 18 | 19 | 20 |
| Structure | 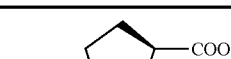 | 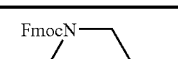 |  | 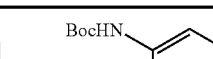 |
| Mw (g/mol) | 413.47 | 427.49 | 401.45 | 502.56 |
| micromol | 36 | 36 | 36 | 36 |
| Weight (mg) | 14.9 | 15.4 | 14.4 | 18.1 |
TABLE 7
| Amino acid used for the 2nd coupling. | | | | |
|---|---|---|---|---|
| Member number | 1 | 2 | 3 | 4 |
| Structure | 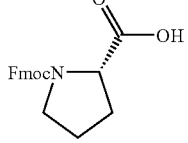 | 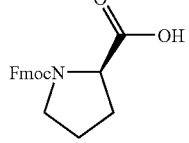 | 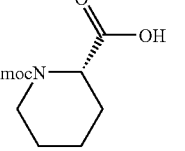 | 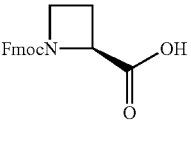 |
| Mw (g/mol) | 337.37 | 337.37 | 351.40 | 323.34 |
| micromol | 36 | 36 | 36 | 36 |
| Weight (mg) | 12.1 | 12.1 | 12.7 | 11.6 |
| Member number | 5 | 6 | 7 | 8 |
| Structure | 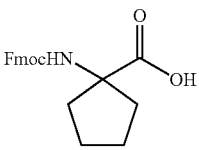 | 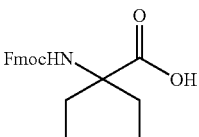 | 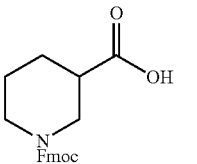 |  |
| Mw (g/mol) | 351.40 | 365.42 | 351.40 | 413.47 |
| micromol | 36 | 36 | 36 | 36 |
| Weight (mg) | 12.7 | 13.2 | 12.7 | 14.9 |
| Member number | 9 | 10 | 11 | 12 |
| Structure | 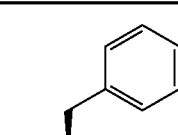 | 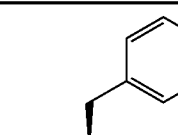 | 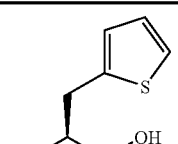 | 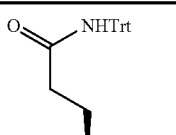 |
| Mw (g/mol) | 405.42 | 387.43 | 393.46 | 610.70 |
| micromol | 36 | 36 | 36 | 36 |
| Weight (mg) | 14.6 | 13.9 | 14.2 | 22.0 |

TABLE 7-continued

| | Amino acid used for the 2nd coupling. | | | |
|---|---|---|---|---|
| Member number | 13 | 14 | 15 | 16 |
| Structure | (Fmoc-Leu-OH) | (Fmoc-Ile-OH) | (Fmoc-Asp(OtBu)-OH) | (Fmoc-4-phenyl-4-piperidinecarboxylic acid) |
| Mw (g/mol) | 353.41 | 353.41 | 411.45 | 427.49 |
| micromol | 36 | 36 | 36 | 36 |
| Weight (mg) | 12.7 | 12.7 | 14.8 | 15.4 |
| Member number | 17 | 18 | 19 | 20 |
| Structure | (Fmoc-4-(Boc-cyclohexylmethylamino)pyrrolidine-2-carboxylic acid) | (Fmoc-Thr(tBu)-OH) | (Fmoc-His-OH) | (Fmoc-Ala-OH) |
| Mw (g/mol) | 548.67 | 397.46 | 477.51 | 311.33 |
| micromol | 36 | 36 | 36 | 36 |
| Weight (mg) | 19.8 | 14.1 | 17.2 | 11.2 |

TABLE 8

| | Amino acids used for the 3rd coupling. | | | |
|---|---|---|---|---|
| Member number | 1 | 2 | 3 | 4 |
| Structure | (Fmoc-Val-OH) | (Fmoc-Leu-OH) | (Fmoc-Ile-OH) | (Fmoc-Thr(tBu)-OH) |
| Mw (g/mol) | 339.39 | 353.41 | 353.41 | 397.46 |
| micromol | 36 | 36 | 36 | 36 |
| Weight (mg) | 12.2 | 12.7 | 12.7 | 14.1 |
| Member number | 5 | 6 | 7 | 8 |
| Structure | (Fmoc-α-methyl-Asp(OtBu)-OH) | (Fmoc-Asn(Trt)-OH) | (Fmoc-Glu(OtBu)-OH) | (Fmoc-cyclohexylglycine-OH) |
| Mw (g/mol) | 411.45 | 596.67 | 425.47 | 379.45 |
| micromol | 36 | 36 | 36 | 36 |
| Weight (mg) | 14.8 | 21.5 | 15.3 | 13.7 |

TABLE 8-continued

Amino acids used for the 3rd coupling.

| Member number | 9 | 10 | 11 | 12 |
|---|---|---|---|---|
| Structure | [His(Boc) with FmocHN, OH, O] | [Dab(Boc) with FmocHN, OH, O] | | |
| Mw (g/mol) | 477.51 | 440.49 | | |
| micromol | 36 | 36 | | |
| Weight (mg) | 17.2 | 15.9 | | |

TABLE 9

Amino acids used for the 4th coupling.

| Member number | 1 | 2 | 3 | 4 |
|---|---|---|---|---|
| Structure | [BocHN-Ala-OH] | [BocHN-D-Ala-OH] | [BocHN-Ser(tBu)-OH · DCHA⁺] | [BocHN-D-Ser(tBu)-OH · DCHA⁺] |
| Mw (g/mol) | 189.21 | 189.21 | 442.63 | 442.63 |
| micromol | 36 | 36 | 36 | 36 |
| Weight (mg) | 6.81 | 6.81 | 15.9 | 15.9 |
| Member number | 5 | 6 | 7 | 8 |
| Structure | [BocHN-Thr(tBu)-OH] | [Boc-Aze-COOH] | [BocHN-Aib-OH] | [Boc-N(Me)-Ala-OH] |
| Mw (g/mol) | 275.34 | Mol. Wt. 323.34 | 203.24 | 203.24 |
| micromol | 36 | 36 | 36 | 36 |
| Weight (mg) | 9.91 | 7.24 | 7.31 | 7.31 |
| Member number | 9 | 10 | 11 | 12 |
| Structure | [BocHN-Abu-OH] | [BocHN-D-Thr(tBu)-OH] | | |
| Mw (g/mol) | 203.24 | 275.34 | | |
| micromol | 36 | 36 | | |
| Weight (mg) | 7.31 | 9.91 | | |

Attachment of "Adhesion Peptide":
Alloc Deprotection of Second "Core" Glycine:

The beads from the 20 wells were all combined in a 50 mL syringe and washed with $CHCl_3$ (5×) and with Ar-degassed $CHCl_3$ containing 5% HOAc and 2.5% NEM (5×). A solution of $Pd(PPh_3)_4$ (3 eq, 0.72 mmol) in Ar-degassed $CHCl_3$ containing 5% HOAc and 2.5% NEM (10 mL) was added to the beads and after a few minutes bobling with Ar the syringe was sealed with parafilm and left for 2 h. The beads were washed with $CHCl_3$ (10×), DMF (10×), MeOH (10×), DMF (20% pip) (2×), DMF (10×). Kaiser test was positive.

Attachment of HMBA Linker
According to standard procedure above.
MSNT Coupling of FmocGlyOH
According to standard procedure above.
TBTU coupling of FmocLys(Fmoc)OH
According to standard procedure above.

Attachment of Adhesion Peptides

Adhesion peptides were synthesized on the Fmoc-protected lysine such that the final beads had two adhesion peptides pr. library molecule. One batch of the library was attached adhesion peptide A, and a second batch with adhesion peptide B.

Adhesion peptide A: (Boc-D-Ala-D-Arg(Pmc)-D-Lys(Boc)-D-Arg(Pmc)-D-Ile-D-Arg(Pmc)-D-Gln(Trt)-Gly-:

Fmoc deprotection of lysine residues: According to the standard procedure.

Coupling: The adhesive peptide was synthesized directly (stepwise) on the library beads using the general SPPS coupling procedure.

Alternative method: The purified peptide (Boc-D-Ala-D-Arg(Pmc)-D-Lys(Boc)-D-Arg(Pmc)-D-Ile-D-Arg(Pmc)-D-Gln(Trt)-L-Gly-OH) (3 eq) was coupled to the lysine $NH_2$ groups using the general SPPS coupling procedure.

Adhesion peptide B: (Fmoc-D-Arg(Pmc)-D-Gln(Trt)-D-Arg(Pmc)-D-Ile-D-Arg(Pmc)-: Analogous to synthesis of adhesion peptide A.

Deprotection of Adhesion and Library Peptides

Final deprotection of protecting groups was performed according to the general procedure described above yielding the TCOB library ready for testing.

Example 4

Assay for Identification of Protein-Protein Interaction (ML-IAP:Smac) Modulators The present assay that is based on the principle: Bioluminescence Resonance Energy Transfer ($BRET^2$) commercial available from Perkin Elmer. One of two interacting proteins is fused to a bioluminescent donor (luciferase, Rluc) and the other protein is fused to a fluorescent acceptor (GFP).

Melanoma Inihitor of Apoptosis Protein (ML-IAP) Probe:

The probe is constructed by PCR amplification of the ML-IAP (GenBank Accession number: NM_139317 (alpha form); NM_022161 (beta form)) from human cDNA libraries (Marathon-Ready cDNA Library of human kidney cell line and a human fetal brain cell line, Clontech Laboratories, Inc.) using the primers livin-F1 (5'-CCA GTG TTC CCT CCA TGG GAC CTA A-3') and livin-R1 (5'-TAA GCC ATC CCC CAC GCC AAG-3') (SEQ ID 27). The ML-IAP cDNA gene fragments are further modified to contain restriction sites by PCR amplification using the primers Livin-F3 (5'-GAT AAG CTT CCA GTG TTC CCT CCA TGG GA-3') (SEQ ID 28), Livin-R3 (5'-TAT GGA TCC AAG GTG CGC ACG CGG CT-3') (SEQ ID 29), and Livin-F4 (5'-GAG AAT TCT CCT AAA GAC AGT GCC AAG TG-3') for full-length ML-IAP and the primers Livin-BIR-F1 (5'-CAT GGT ACC ATG ACA GAG GAG GAA GAG GAG-3') and Livin-BIR-R1 (5'-GC TGG ATC CGG GTC CCA GGA GCC CAG-3') (SEQ ID XX) for the BIR domain of ML-IAP. The restriction enzyme-treated amplifcons are ligated in the BRET2 vectors (obtained from Perkin Elmer, Inc.) to produce N- and C-terminal in-frame fusions to GFP and Rluc.

Smac Probe:

The probe is constructed by ligating restriction enzyme treated PCR amplification products of the cDNA for human Smac (GenBank Accession NM_019887 (variant 1); NM_138929 (variant 3)) in to the BRET2 vectors (obtained from Perkin Elmer, Inc.) to produce C-terminal in-frame fusions to GFP and Rluc, respectively. The following primers are used for PCR: Smac-F1 (5'-GCG CTG CAC AAT GGC GGC TCT-3') (SEQ ID 31), Smac-R1 (5'-GCA CTC ACA GCT CAC AAA GGC GTC T-3') (SEQ ID 32), Smac-F3 (5'-GAT GGT ACC CGC TGC ACA ATG GCG GCT CT-3') (SEQ ID 33), and Smac-R3 (5'-CGT GGA TCC TCA CGC AGG TAG GCC TCC-3') (SEQ ID 34). Cytosolic expression of biologically Smac is achieved by constructing an ubiquitin-smac fusion as described by Allison M. Hunter, Dan Kottachchi, Jennifer Lewis, Colin S. Duckett, Robert G. Korneluk, and P. Liston. A Novel Ubiquitin Fusion System Bypasses the Mitochondria and Generates Biologically Active Smac/DIABLO. J. Biol. Chem. 278 (9):7494-7499, 2003.

Cell Line Establishment:

Cells are co-transfected with the BRET fusions of ML-IAP and Smac using standard procedure for Fugene6 transfection. Cells are put under G418 and zeocin selection for 4 weeks to obtain a cell line stably expressing the two genes.

Selection of Stable Cells:

The HeLa cell line stably expressing both probes are sorted into a microtitre plate (one cell per well) for high GFP fluorescence using a Fluorescence Activated Cell Sorter. The sorted cells are grown for a week, and split into a plate that is optimized for bio-luminescence. Final cell-clones are selected, after addition of the luciferase substrate, DeepBlueC (Perkin Elmer), for high luminescence (detected with a PolarStar, BMG).

Bead/Cell Preparation:

HeLa/mammalian cells are cultured on PEGA beads displaying adhesion peptide (as described in step 13, example 2) and respectively 1) Negative control (PEGA beads with adhesion peptide, and a compound with no activity), 2) Positive control (PEGA beads with adhesion peptide, and a control compound, which is described in example 20 of WO2004/005248 that disrupts the ML-IAP:Smac interaction and 3) Library compounds (PEGA beads with adhesion peptide, and screening compounds prepared as described in example 2). The three cultures are handled separately in each their culture flask.

Cells are trypsinized and mixed with the PEGA beads in growth medium (DMEM containing 10% FCS, in the proportion 4000 cells/bead and app. 50 ml growth medium/5000 beads. Culture flasks are placed on a Magnetic stirring platform (Techne) designed for cell culture in suspension and incubated at 37°, 5% $CO_2$ for 16-24 hrs using spinning interval 30 rpm, 3 min stirring, 10 min pause.

Cell-coated beads are treated as follows:
1) Positive control (low BRET signal): 50 ml Growth medium+approx. 5000 cell-coated control beads.
2) Negative control (high BRET signal): 50 ml Growth medium+approx. 5000 cell-coated control beads 3) Screening library (eg. 100.000 compounds): 1000 ml Growth medium+approx. 100.000 cell-coated library beads.

The three culture flasks are placed on a Magnetic stirring platform (Techne) designed for cell culture in suspension and incubated at 37°, 5% $CO_2$ for 2-24 hrs using spinning interval 30 rpm, 3 min stirring, 10 min pause. The cell-coated beads are illuminated with UV light (365 nm) for 1-30 min for obtaining a partial release of the library compounds. The illuminated beads are further incubated at 37°, 5% $CO_2$ for 15 min. Beads, now covered with cells, are allowed to sediment for 10 min (no centrifugation needed) and the supernatant is removed using a 50 ml pipette. The beads are treated with 10 ml 99% EtOH per 5000 beads, mixed gently and left for 15 min. Beads are washed w. 10 ml PBS/5000 beads×3 by allowing sedimentation for 10 min between each wash. Cells are now preserved and fixed to the beads.

Bead Sorting:

A Fluorescence Activated Bead Sorter (FABS) equipped with filters for BRET detection and sorting capability into 96 well plate is used to identify and isolate positive hit beads.

The luciferase substrate, DeepBlueC is injected into the flow stream to emit luciferase-mediated luminescence.

The FABS is calibrated to identify and isolate positive hit beads (decreased BRET signal) by determining the dynamic range of the assay using positive control beads prepared as described in above as Smax (maximum response) and negative control beads comprising only cell adhesion peptide as 5 min (minimum response).

Positive hits are separated into each their well of a 96 well plate and are hereafter ready for cell and adhesion peptide detachment, compound elucidation, re-synthesis and re-test as well as test for effects in other assays.

Individual beads are analysed in a BRET-compatible microplate reader using 410-80 (370-450 nm) and 515-30 (500-530 nm) bandpass filters for dual emission measurements of Rluc-luminescence and GFP-fluorescence, respectively. The luciferase substrate, DeepBlueC, is added by an on-board injector in the microplate reader. The BRET-signal for the protein-protein interation is calculated as the ratio of emission at 515 nm and emission at 410 nm.

Example 5

Caspase Activity Assay

Inhibitor of apoptosis proteins (IAPs) interact with caspases to inhibit their activation and thereby cause a repression of apoptosis. Preferred compounds are compounds, which can bind to IAP with a higher affinity than caspase and, in turn, relieve IAP-mediated caspase-inhibition. A screening assay is established that measures caspase activation in response to an apoptosis inducing signal (e.g. staurosporine or UV light) and in the presence of library compounds with putative IAP-binding activity.

The assay is based on measurements of caspase activity in whole mammalian cells (HeLa/SK-Mel28) cultured on PEGA beads displaying adhesion peptide (as described in Step 13, example 2) and respectively 1) Negative control (PEGA beads with adhesion peptide, and a compound with no activity as the library component, e.g. [4-(1-acetamido-ethyl)-2-methoxy-5-nitrophenoxy]butanoic acid linked to the bead via the second glycine. 2) Positive control (PEGA beads with adhesion peptide, and a control peptide that disrupts the ML-IAP:Smac interaction as the library component e.g. the compound of Example 20 in WO2004/005248 and 3) Library compounds (PEGA beads with adhesion peptide, and screening compounds which are prepared essentially as described in example 2). The three cultures are handled separately in each their culture flask. Caspase activity is measured in bead-attached whole cells by incubating the cells with a fluorogenic caspase substrate with a quenching leaving group DEVD-Rh110-C8, described in the following publication: Sui Xiong Cai, Han Zhong Zhang, John Guastella, John Drewe, Wu Yang, and Eckard Weber. Design and synthesis of Rhodamine 110 derivative and Caspase-3 substrate for enzyme and cell-based fluorescent assay. Bioorganic & Medicinal Chemistry Letters 11 (1):39-42, 2001 and in the patent: U.S. Pat. No. 6,342,611 B1 (Jan. 29, 2002, Cytovia, Inc. San Diego, Calif.). A fluorogenic counter stain with different emission properties is applied to correct for cell mass content on the individual beads.

Bead/Cell Preparation:

Cells are trypsinized and mixed with the PEGA beads in growth medium (DMEM containing 10% FCS, in the proportion 4000 cells/bead and app. 50 ml growth medium/5000 beads.

The beads/cells are placed in three culture flasks and placed on a Magnetic stirring platform (Techne) designed for cell culture in suspension incubated at 37°, 5% $CO_2$ for 16-24 hours using spinning interval 30 rpm, 3 min stirring, 10 min pause.

Cell-coated beads are treated as follows:
1) Positive control: 50 ml Growth medium+approx. 5000 Positive control beads. 2) Negative control: 50 ml Growth medium+approx. 5000 Negative control beads.
3) Screening library (eg. 100.000 compounds): 1000 ml Growth medium+approx. 100.000 cell-coated Library compound beads.

Screening Procedure:

The cell-coated beads are illuminated with UV light (365 nm) for 1-30 min for obtaining a partial release of the library compounds. The three culture flasks are placed on a Magnetic stirring platform (Techne) designed for cell culture in suspension and incubated at 379, 5% CO2 for 3-6 hrs.

The beads are then allowed to sediment for 10 min (no centrifugation needed) and the growth medium is removed using a 50 ml pipette. 1 ml medium containing the fluorogenic caspase substrate and reagent buffer is added to the beads. The beads are incubated without stirring at 37°, 5% CO2 for 0.5-5 hours. The beads are treated with a fixative, such as 10 ml 99% EtOH per 5000 beads, or formaldehyde, acetone or zinc-based fixatives, mixed gently and left for 15 min.

Beads are washed w. 10 ml PBS/5000 beads ×3 by allowing sedimentation for 10 min between each wash. Cells are now preserved and fixed to the beads.

Bead Sorting:

A Fluorescence Activated Bead Sorter (FABS) equipped with 488 nm excitation filters and 500-550 nm emission filter for rhodamine-110 measurements and sorting capability into 96 well plate is used to identify and isolate positive hit beads.

The FABS is calibrated to identify and isolate positive hit beads (increased caspase activity) by determining the dynamic range of the assay using positive control beads with apoptosis induced cells to determine the Smax (maximum response) and negative control beads with uninduced cells as 5 min (minimum response).

Positive hits are separated into each their well of a 96 well plate and are hereafter ready for compound elucidation, re-synthesis and re-test as well as test for effects in other assays.

Microscopy:

An alternative to FABS-based selection of positive hit beads is epifluorescence microscopy using standard FITC filters (excitation 480±15 nm, emission 535±20 nm) for visualization of rhodamine 110 fluorescence. The microscope is equipped with micromanipulators for extraction of positive hit beads.

Example 6

Identification of Compound

Once a resin bead is selected, the cells may be cleared off the beads either by extensive washing or in case of HMBA-linked adhesion peptides by treatment with 0.1 M NaOH followed by washing (example 7). The library compound comprised within the bead may then be identified. Selected bead(s) are washed and swelled in a small drop of pure water and irradiated for 30 min. with an OMNILUX E-40 (400 W UV lamp, 365 nm, #89514005, Steinigke Showtechnic GmbH, Germany).

The compound is identified with advanced mass spectrometry combined with single bead and/or nano-scale NMR techniques. For example advanced MS may be ES MS-MS analysis on a MicroMass QTOF Global Ultima mass spectrometer (mobile phase 50% $CH_3CN$ (aq), 0.1 µL/min) employing a linear ramping of the collision energy. The spectra are analyzed by generating the exact mass differences between fragment ions and tabulated to provide the fragmentation pathway and from that the structure of the compound released from the selected bead is elucidated.

In several cases analysis provides several possible structures. In these cases resynthesis and conformation of fragmentation pattern can unambiguously assign the selected compound.

Example 7

Apoptosis Assay for Membrane Integrity, GFP/Eth Based

Background:
Membranes of apoptotic cells become permeable over time. GFP expressing U2OS cells are used to monitor this phenomenon by measuring the decrease in total GFP fluorescence after induction of apoptosis. In addition cells are stained with Ethidium bromide, which stains nucleus (DNA), but only in membrane permeable cells. By ratioing the fluorescence signal from the two dyes we have developed a reliable "on bead" membrane integrity assay.

Preferred compounds according to the invention are compounds wherein a high apoptosis rate is observed in cells attached to resin beads linked to the compound.

Detailed Procedure:
Resin beads comprising a test compound (hereinafter designated library beads) and control beads are dissolved in 5 ml EtOH and incubated for 30-60 min (to obtain sterile beads). 3 ml EtOH swelled beads corresponds to app. 45.000 beads.

Beads are washed 3 times in 5 ml Growth medium (Hams F12 w. FCS 10% and penicillin 100 u/ml, Streptomycin 0.1 mg/ml).

Beads are divided into an appropriate number of 14 ml Nunc tubes having app. 7500 beads/tube. Growth medium is removed.

U2OS-GFP cells are loosened using EDTA (standard procedure known to the skilled person) and adjusted to 0.8×10E6 cells/ml Growth medium U2OS-GFP cells are divided into an appropriate number of 14 mL vials in a volume of 4.5 ml in each. U2OS-GFP cells are UV illuminated for 3 min.

Each vial with EtOH sterilized beads is added 4.5 ml U2OS-GFP cell suspension and incubated 3-4 hrs. Tilt gently every 15 min for the first 1 hrs Beads now covered with U2OS-GFP cells are divided into eppendorf vials, 5 vials pr. 14 ml tube.

Growth medium is removed from beads/U2OS-GFP cells in eppendorf tubes and replaced with 750 µl fresh Growth medium pH 7.0 (adjusted with HCl and tested using pH strips with 0.2 pH value steps). To one portion (appr. 1500 beads) of negative control beads/U2OS-GFP cells 2CX2.201 40 µM is included in the 750 µl Growth medium (serves as positive 2CX2.201 control)

UV illumination for 2 min of all eppendorf vials (8-10 vials at a time placed in a petri dish)

Beads/U2OS cells are incubated under standard cell culture conditions for 1 hr.

STS 30 nM is added to all vials (except Smax) by adding 250 µl Growth medium w. STS 120 nM to 750 µl already in the vial (2CX2.201 is diluted 1:¼~30 uM)

To one portion of negative control beads and/or library beads STS 1 uM is added instead of 30 nM=Smax.

Incubate for 24 hrs under standard cell culture conditions

Growth medium is replaced with 0.5 ml fresh Growth medium w. Ethidium Bromide (Eth-d1) 2 µM and incubated for 30 min under standard cell culture conditions.

Growth medium/Eth-d1 is replaced with 1 ml Growth medium+Acid Red (AR) 50 µM and incubated for 30 min under standard cell culture conditions.

FABS instrument is calibrated according to 5 min and Smax of the control beads and cut off region is set corresponding to the upper fraction of Smax or library beads themselves. Laser line: 488 nM is used.

Library beads are sorted using settings described above.

Bead/Control Set-Up:

| | |
|---|---|
| Negative control beads | Smin |
| Negative control beads + 2CX2.201 40/30 µM | Pos 2CX2.201 control |
| 2CX2.201/2CX4.401 beads | Control, UV illumination |
| Library beads + 2CX2.201 40/30 µM | Pos control |
| Library beads + STS 1 µM | Smax |
| Library beads | Screening |

2CX2.201 is the compound described in Example 20 of WO2004/005248

2CX4.401 is a compound of the structure

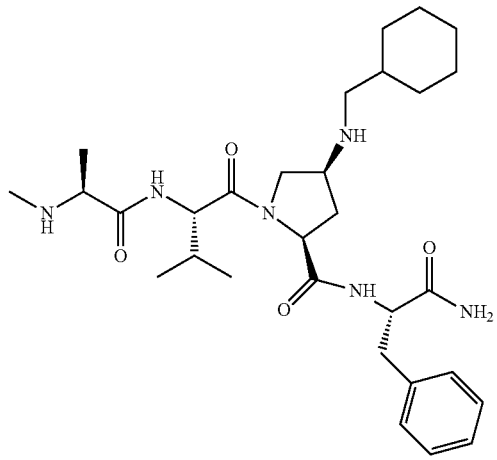

Figure 3:
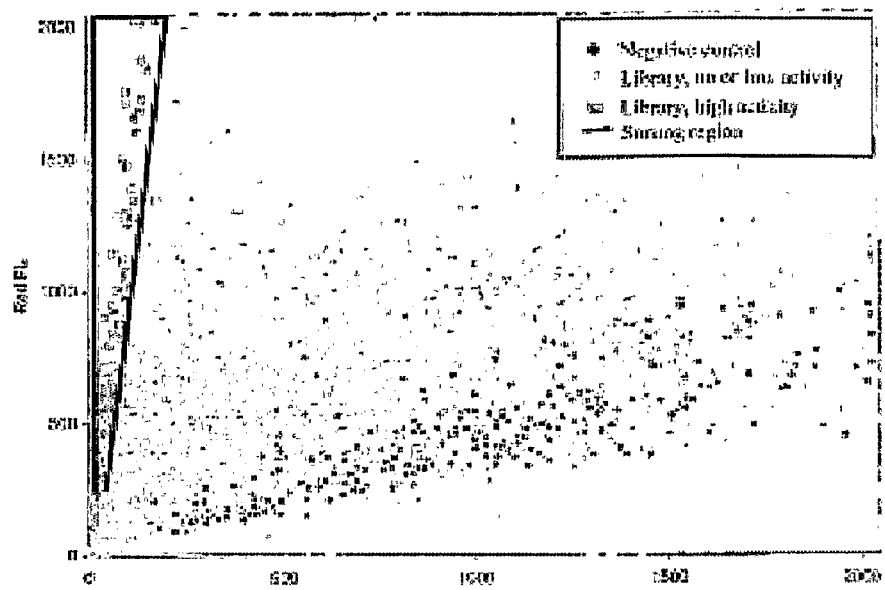
FIG. 3 shows the result of a FABS analysis of resin beads with test compounds performed as described in Example 7.

FIG. 3 discloses the result of a FABS analysis performed as described above. Resin beads within the framed triangle were selected as resin beads comprising preferred compounds. The test compounds attached to said resin beads are identified as described in Example 6.

Example 8

Xenograft Studies

1. Background.

Compounds 2CX2.201 and 2CX4.401 are as described in Example 7.

Efficiency of the compounds in treatment of colon cancer was investigated.

It has been demonstrated that 2CX2.201 and 2CX4.401 penetrate into cells, inhibits IAPs and promote apoptosis in primary colon cancer cells from patients and in colon cancer lines (i.e. HT29) and that 2CX2.201 and 2CX4.401 show a high degree of stability in serum from mice and man.

2. Aim.

The aim of this study is to demonstrate whether the IAP-inhibitors 2CX2.201 and 2CX4.401 inhibit apoptosis and the growth of cancer cells in an in vivo xenograft model.

3. Materials and Methods 3.1 Animals.

Female athymic nude BALB/c mice (BALB/cABom-Foxn1$^{nu}$, CA.Cg-Foxn1$^{nu}$) are obtained from Taconic Ltd, Ry, Denmark and maintained in the animal facility. Animals are approximately 6 weeks old with an initial body weight of 17-18 g when used for the experiments. The mice are housed in microisolators (filter top cages, Tecniplast, Buguggiata, Italy) under pathogen-free conditions with a 12-h light/12-h dark schedule and fed autoclaved standard chow (Altromin #1324, Lage, Germany) and water ad libitum throughout the experiment. All animals are handled under sterile conditions and maintained in a separate facility. The Danish Experimental Animal Inspectorate has approved the experimental protocol and all animal experiments are performed according to the ethical standards required by the UKCCCCR Guidelines {UKCCCR 1998}. During the study blood samples is taken one time per week. The number of animals per group (control-treatment) should be 8 animals at a minimum. Thirty-fifty percent more animals are inoculated with cells than needed in the study in order to be able to exclude animals in which there is no tumour take—i.e. the tumour fails to establish and grow progressively.

3.2 Cell Culture.

The human colorectal adenocarcinoma cell line HT-29 (HTB-38) has been obtained from the American Type Culture Collection (ATCC) Manassas, Va., USA. Tumour cells growing exponentially are harvested by brief incubation with 0.05% Trypsin-EDTA solution suspended in new medium for injection.

3.3 In Vivo Experimental Protocol.

Tumour xenografts are initiated by subcutaneous (s.c.) injection of $10^7$ cells into the left flank of nude mice. Three days later, tumours are expected to have grown to a volume of approximately 60-70 mm$^3$. The animals are divided into six groups with approximately equal average tumour volumes and randomly allocated to receive 1) 0.4 ml saline or
2) the test-compound 2CX2.201 in osmotic pumps (Alzet Osmoic Pumps; cat.#: 2004) in a dose of 0.0625 mg/h.
3) the test-compound 2CX2.201 in osmotic pumps in a dose of 0.0625 mg/h and paclitaxel (taxol) at a dose of 25 mg/kg once a week by a subcutaneously injection.
4) Paclitaxel (taxol) in a dose of 25 mg/kg once a week by a subcutaneously injection.
5) the test-compound 2CX4.401 in osmotic pumps in a dose of 0.0625 mg/h.
6) the test-compound 2CX4.401 in osmotic pumps in a dose of 0.0625 mg/h and paclitaxel (taxol) at a dose of 25 mg/kg once a week by a subcutaneously injection.

3.4 Monitoring.

Tumour volume, food consumption, body weight is measured twice a week. Blood sample is taken once per week. Animals with tumours that do not show exponential growth, indicating that the tumour do not grow, are excluded from the study. Evaluation of tumour growth: The tumours are measured every 3-4 day with a calliper. Baseline tumour weight are calculated by using the following formula mg=(L×W$^2$)/2 where L=length, W=width and these are perpendicular to each other {Teicher BA 1997}.

3.5 Termination of Study.

At 21-30 days after inoculation, mice are sacrificed after anaesthesia with sodium barbital (50 mg/kg i.p.), and blood is drawn 3 minutes later from the retro orbital venous plexus. Serum is extracted by centrifugation after clotting. Serum is stored at −80° C. until measurements are performed. The animals are euthanised by cervical dislocation and tumour and liver from each animal is careful removed and weighted. Pieces of liver and tumour are snap-frozen in liquid nitrogen; ⅓ for purification of mRNA, ⅓ for analyses of in situ apoptosis activation using the In Situ Cell Death Detection Kit (POD; cat.#: 11 684 817 001) and the rest tumour sample is fixed in 4% buffered neutral formalin for histological examination.

3.6 Analysis of Serum for CEA.

Determination of Carcino-Embryonic Antigen (CEA) in serum. The amount of CEA in serum from mice inoculated with HT-29 was determined by a clinical assay kit (Wallac, Turku, Finland).

3.7 Statistical Methods.

All data are expressed as the mean±SEM, and statistical analyses of the tumour data are performed using t-test. All P values are based on two-sided hypothesis testing.

3.8 Materials.

The following reagents are obtained:
Paclitaxel (Sigma Chemical Co.; cat.#: T7402).
Cremophor EL (Sigma Chemical Co.; cat.#: C5135).
Alzet Osmotic Pumps (cat.#: 2004).
2CX2.201.
2CX4.401.

Figure 4:
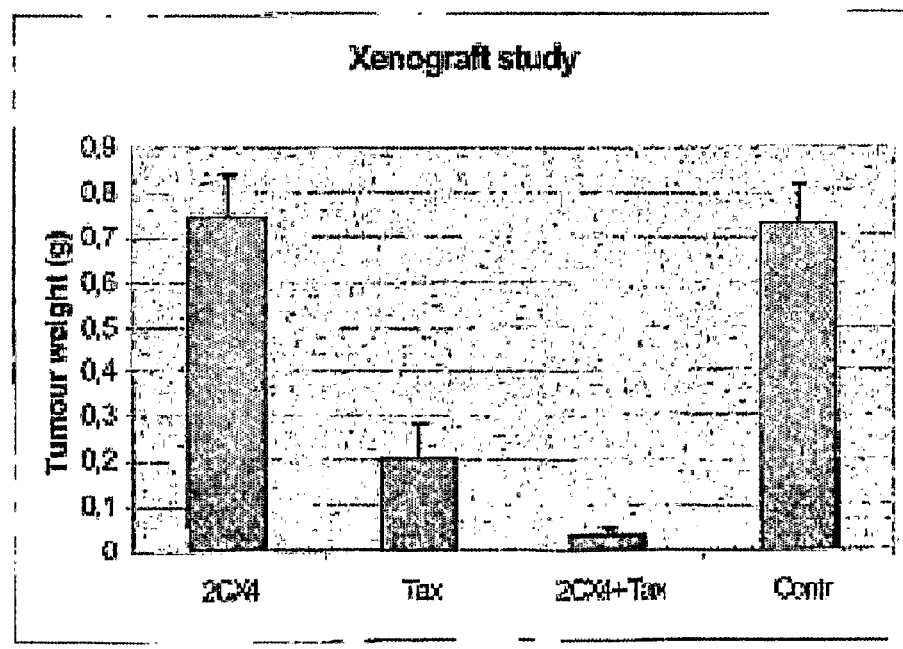
FIG. 4 shows tumour weight in mice after Xenograft studies as described in Example 8.

FIG. 4 discloses results of a xenograft study that was finalized 29 days after inoculation of the mice. 2CX4.401 (designated 2CX4) significantly potentiated the effect of Paclitaxel. After 29 days it is observed that the combined treatment decreased the tumour weight to approx. 15% of that observed with Paclitaxel alone. 2CX4.401 does not affect tumour growth when given to the animals in mono-therapy. This feature is in agreement with the theory that the specific apoptosis induction in cancer treatment should not directly induce tumour cell death; but should prime cancer cells for destruction.

Administration of the drug 2CX2.201 i.v. to mice at a dose of 30 mg/kg causes immediate death of the animals. Corresponding dosing 100 mg/kg i.p. have similar effect. Dosing the drug 2CX2.201 in a minipump at a rate of 1.5 mg/kg per hour or 3 mg/kg per hour causes deposit of fibrous material around the dosing area. Furthermore the animals subjected to this treatment had significant weight loss within 24 hours. It can be concluded that several adverse effects are connected to the use of 2CX2.201 in vivo.

Example 9

Pull Down Experiments

Background:

Beads displaying compound 2CX2.201 or 2CX4.401 respectively are compared with regard to their ability to bind and pull down one member of the IAP family, XIAP from cell lysates prepared from various tissues.

Preferred compounds according to the invention are compounds wherein a high apoptosis rate observed in intact cells is associated with a high affinity for members of the IAP family, such as XIAP. For example, in one embodiment, the affinity of a compound of the present invention is comparable or at least as high as the affinity of the endogenous AVPF peptide. Preferably, the compound according to the present invention has a higher affinity for a member of the IAP family, such as XIAP, than 2CX2.201 does.

Figure 5A:
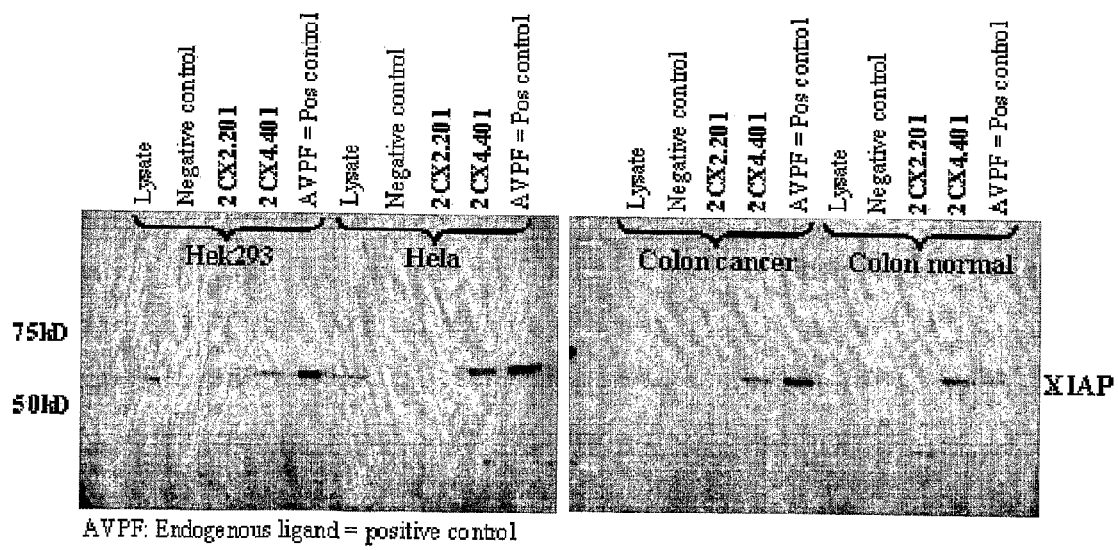
FIG. 5a shows pull down experiments from various tissues as described in Example 9.
Figure 5B:
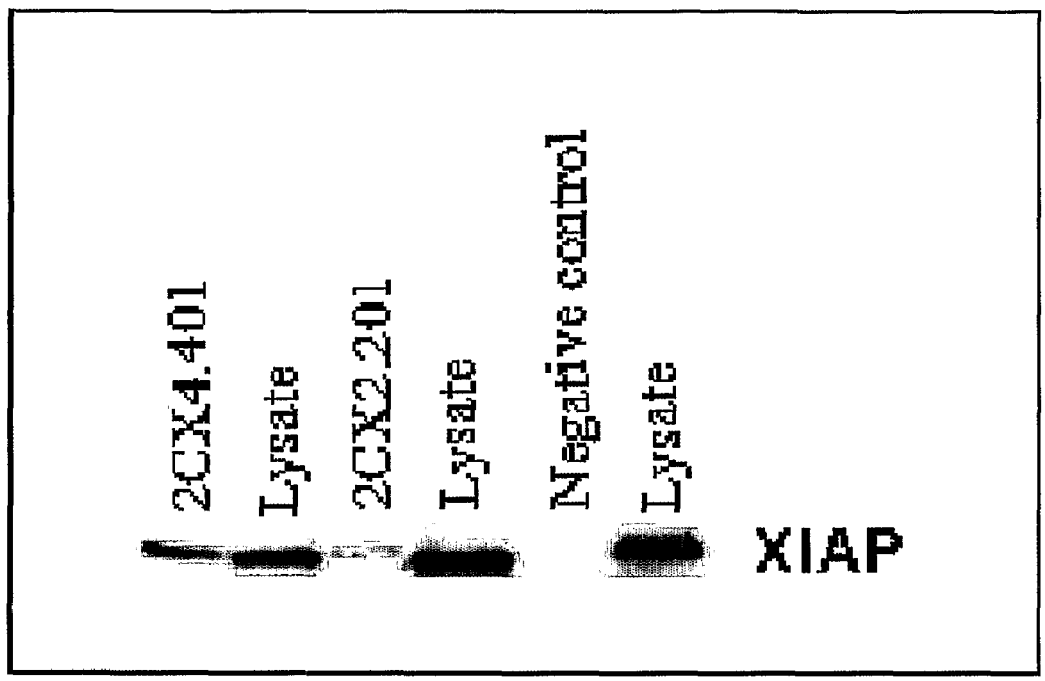
FIG. 5b shows an additional pull down experiment as described in Example 9.

Detailed Procedure:
Test Beads:
Positive control resin beads carrying a tetra-peptide (H-Ala-Val-Pro-Phe-Bead) mimicking the N-terminal part of Smac that binds to BIR3 domain of XIAP was prepared. The method of preparation was analogous to the general procedure described in example 2 with the change that only the four specific peptides were included in each of the four couplings and that the split and mix step was omitted.
Resin beads carrying 2CX2.201 was prepared as described above.
Resin beads carrying 2CX4.401 was prepared as described above.
Lysate Preparation:
Hek293 and Hela: Cells are scraped off the plate in Phosphate Buffered Saline (PBS) at 4° C.
Colon tissue: Is blended into a homogeneous suspension in PBS at 4° C.
All cell suspensions are centrifuged for 10 min at 3000 rpm and supernatant is discarded.
Pellet is re-suspended in lysis buffer (50 mM Tris-HCL, 1 mM EGTA, 1 mM EDTA, 1% Triton-X W/W, 1 mM Sodium orthovanadate, 50 mM Sodium fluoride, 5 mM Sodium pyrophosphate, 1 mM MDTT, "Complete" (protease inh.) One tablet for 50 ml)
Incubate for 20 min at 4° C.
Centrifuge at 32.000 G for 30 min, 4° C.
Move supernatant to new vial (discard pellet)
Measure protein concentration
Pull Down:
Bead/lysate ratio: 20 ul beads/10 mg lysate (equivalent to one pull down)
Beads are washed in 1 ml lysis buffer×2
Lysate+beads are mixed and incubated for 1 hrs at 4° C., shaking
Beads are washed ×4 in 1 ml Lysis buffer w. 0.15M NaCl
Beads are wash ×2 in 1 ml Buffer A (50 mM Tris pH 7.5, 0.1 mM EGTA, 1 mM DTT
60 ul SDS loading buffer is added (1:4 SDS/H2O) XIAP lysate control: 20 ul SDS loading buffer+20 ug lysate
Incubate at 100° C. for 5 min
Electrophoresis:
Load 30 ul of each sample to gel
Run gel (Invitrogen, NuPAGE 10% Bis-Tris Gel, 1 mm×10 well: NPO301 Box) in running buffer (MES/H20 1:20) for 1 hrs at 200V
Western:
Proteins are blotted on membrane (wet, 200V, 1.5 hrs)
Membrane is incubated for 30 min in TBS-T (Tris Buffer Saline w. 0.2% Tween-20)+10% skim milk
Membrane is incubated with 1 ml XIAP antibody (Purified mouse anti-hILP/XIAP Mab, BD Transduction Laboratorie #610717) diluted 1:500 in TBS-T for 3 hrs. During incubation the membrane is covered with plastic film
Membrane is washed thoroughly in TBS-T buffer w. 10% skim milk
Membrane is added secondary antibody (Mol. Probes. #A-21059
Goat anti-mouse Alexa fluor 680) diluted 1:10.000 in TBS buffer w. 10% skim milk and incubated for 40 min at RT
Membrane is washed ×8 in TBS-T buffer
Membrane is scanned using a Li-cor odyssey scanner equipped with appropriate filters for the Alexa fluor 680.
Results:
FIG. 5a discloses the ability of beads carrying 2CX4.401, 2CX2.201 and AVPF to pull-down one member of the IAP family, XIAP. It can be concluded that 2CX4.401 is able to pull down XIAP from all tested cell types to approximately the same degree as the endogenous AVPF peptide, In contrast, pull down of XIAP by 2CX2.201 is below detection limit under the given conditions. FIG. 5b showed pull down of XIAP by both 2CX4.401 and 2CX2.201 but with weaker effect of 2CX4.401. To increase sensitivity in this experiment, the exposure time was prolonged compared to experiment in FIG. 5a.

It can be concluded that 2CX4.401 interacts with XIAP with a significant higher affinity than that of 2CX2.201.

Abbreviations:

| | |
|---|---|
| HGF: | Hepatocyte Growth Factor |
| NGF: | Nerve Growth Factor |
| PDGF: | Platelet Derived Growth Factor |
| FGF: | Fibroblast Growth Factor |
| EGF: | epidermal Growth Factor |
| GH: | Growth hormone |
| TRE: | TPA Response Element |
| SRE: | serum response element |
| CRE: | cAMP response element |
| AcN: | acetonitril; |
| Boc: | tert-butoxycarbonyl; 'Bu: tert-butyl; |
| BTC: | Bis-trichloromethylcarbonate, triphosgene; |
| DCM: | dichloromethane; |
| DIPEA: | Diisopropylethylamine, Hünig's base; |
| DMAP: | 4-Dimethylaminopyridine |
| DMF: | dimethylformamide; |
| EDC: | 1-(3-Dimethylaminopropyl)-3-ethyl-carbodiimid hydrochloride |
| Fmoc: | 9-fluorenylmethoxycarbonyl; |
| HMBA: | 4-hydroxymethylbenzoic acid; |
| Holmes linker: | [4-(1-amino-ethyl)-2-methoxy-5-nitrophenoxy]-butanoic acid |
| Q-TOF MS: | quadrupole time-of-flight mass spectrometry; |
| MeIm: | N-methyl imidazole; |
| MSNT: | 1-(mesitylene-2-sulphonyl)-3-nitro-1H-1,2,4-triazole; |
| NEM: | N-ethyl morpholine; |
| PEGA: | polyethylene glycol-polydimethyl acrylamide resin; |
| Pfp: | pentafluorophenyl; |
| Pip: | Piperidine |
| Pmc: | 2,2,5,7,8-pentamethylchroman-6-sulfonyl; |
| RP-HPLC: | reversed phase high pressure liquid chromatography; |
| SPPS: | solid phase peptide synthesis; |
| TBTU: | O-(benzotriazol-1-yl-N,N,N',N'-tetramethyluronium tetrafluoroborate; |
| TCOB: | Two-compound-one-bead |
| TEOF: | Triethylorthoformate; |
| THF: | tetrahydrofuran |
| TFA: | trifluoro acetic acid; |
| Trt: | Trityl. |

The invention claimed is:
1. A compound having the formula:

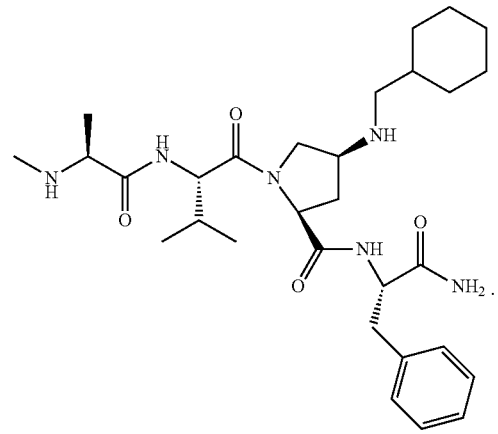

2. A composition comprising the compound according to claim 1 and an anticancer agent.

3. A kit-of-parts comprising the compound according to claim 1 and an anticancer agent.

* * * * *